(12) United States Patent
Rulison et al.

(10) Patent No.: US 9,945,781 B2
(45) Date of Patent: Apr. 17, 2018

(54) ANALYTICAL DEVICES HAVING DICHROIC PRISM ARRAYS

(71) Applicant: Pacific Biosciences of California, Inc., Menlo Park, CA (US)

(72) Inventors: Aaron Rulison, Los Altos, CA (US); Mark McDonald, Milpitas, CA (US); Paul Lundquist, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 15/407,443

(22) Filed: Jan. 17, 2017

(65) Prior Publication Data
US 2017/0167979 A1    Jun. 15, 2017

Related U.S. Application Data

(63) Continuation of application No. 14/289,905, filed on May 29, 2014, now Pat. No. 9,581,550.

(60) Provisional application No. 61/829,827, filed on May 31, 2013.

(51) Int. Cl.
| | | |
|---|---|---|
| *G01N 21/64* | (2006.01) | |
| *G02B 27/10* | (2006.01) | |
| *G02B 5/04* | (2006.01) | |
| *C12Q 1/68* | (2018.01) | |

(52) U.S. Cl.
CPC ....... *G01N 21/6452* (2013.01); *C12Q 1/6874* (2013.01); *G01N 21/6428* (2013.01); *G02B 5/045* (2013.01); *G02B 27/1013* (2013.01); *G01N 2021/6471* (2013.01); *G01N 2021/6478* (2013.01); *G01N 2201/0633* (2013.01)

(58) Field of Classification Search
None
See application file for complete search history.

(56) References Cited

U.S. PATENT DOCUMENTS

| | | | |
|---|---|---|---|
| 6,049,404 A | * | 4/2000 | Wu .................. G02B 6/272 385/16 |
| 7,056,661 B2 | | 6/2006 | Korlach et al. |
| 7,170,050 B2 | | 1/2007 | Turner et al. |
| 7,486,865 B2 | | 2/2009 | Foquet et al. |

(Continued)

*Primary Examiner* — Shawn Decenzo
(74) *Attorney, Agent, or Firm* — Robert H. Reamey

(57) ABSTRACT

Apparatus, systems and methods for use in analyzing discrete reactions are provided. The analytical devices of the invention use an array of nanoscale regions (a chip) that has discrete patches, for example, patches of nanoscale regions. In some embodiments an analytical system is provided that has an analysis chip with an array of patches, each of the patches comprising nanoscale regions that emit fluorescent light when illuminated. The system has a two-dimensional (x, y) array of dichroic prisms, each prism comprising a dichroic element that diverts illumination light up in the z dimension of the array to a patch on the analysis chip above it. Each dichroic element transmits fluorescent light emitted by the patch that it illuminates, whereby the emitted light from each patch passes down through each dichroic prism. The analytical system also has a detector below the array of dichroic prisms that detects the transmitted fluorescent light. Such systems are useful for monitoring many analytical reactions at one time including single molecule sequencing reactions.

18 Claims, 13 Drawing Sheets

(56) References Cited

U.S. PATENT DOCUMENTS

| | | |
|---|---|---|
| 7,805,081 B2 | 9/2010 | Lundquist et al. |
| 7,820,983 B2 | 10/2010 | Lundquist et al. |
| 7,907,800 B2 | 3/2011 | Foquet et al. |
| 8,023,162 B2* | 9/2011 | Kain ............... C12Q 1/6837 250/208.1 |
| 8,143,030 B2 | 3/2012 | Maxham et al. |
| 8,247,216 B2 | 8/2012 | Zaccarin et al. |
| 8,264,687 B2* | 9/2012 | Lundquist ............... G01J 3/02 356/417 |
| 8,274,040 B2 | 9/2012 | Zhong et al. |
| 8,304,191 B2 | 11/2012 | Eid et al. |
| 8,318,094 B1 | 11/2012 | Bayandorian et al. |
| 8,335,029 B2 | 12/2012 | Monadgemi |
| 8,465,699 B2 | 6/2013 | Fehr et al. |
| 8,467,061 B2 | 6/2013 | McCaffrey et al. |
| 9,372,308 B1 | 6/2016 | Saxena et al. |
| 2004/0184960 A1* | 9/2004 | Tanaami ............ G01N 21/6428 422/82.05 |
| 2006/0197032 A9* | 9/2006 | Oostman, Jr. ............. G01J 3/02 250/458.1 |
| 2008/0080059 A1 | 4/2008 | Dixon et al. |
| 2009/0118129 A1 | 5/2009 | Turner |
| 2011/0183409 A1 | 7/2011 | Newby et al. |
| 2011/0278475 A1 | 11/2011 | Lundquist et al. |
| 2012/0021525 A1 | 1/2012 | Fehr et al. |
| 2012/0242960 A1* | 9/2012 | Oiwa ..................... G02B 27/48 353/31 |
| 2015/0268474 A1* | 9/2015 | Cheng ................. G02B 27/225 359/633 |
| 2016/0091705 A1* | 3/2016 | Ben Ezra ............. G02B 21/361 348/79 |
| 2016/0374564 A9* | 12/2016 | Dreher ..................... A61B 3/10 600/319 |

* cited by examiner

ANALYTICAL DEVICES HAVING DICHROIC PRISM ARRAYS

CROSS-REFERENCE TO RELATED APPLICATIONS

This application is a continuation of U.S. patent application Ser. No. 14/289,905 filed on May 29, 2014, which claims the benefit of U.S. Provisional Application No. 61/829,827, filed May 31, 2013, which is incorporated herein by reference in its entirety for all purposes.

STATEMENT REGARDING FEDERALLY SPONSORED RESEARCH

Not Applicable.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

Nucleic acid sequencing, in particular, DNA sequencing is an important analytical technique critical to generating genetic information from biological organisms. The increasing availability of rapid and accurate DNA sequencing methods has made possible the determination of the DNA sequences of entire genomes, including the human genome. DNA sequencing has revolutionized the field of molecular biological research. In addition, DNA sequencing has become an important diagnostic tool in the clinic, where the rapid detection of a single DNA base change or a few base changes can be used to detect for example, a genetic disease or cancer.

In optical analyses, increasing multiplex often poses increased difficulties, as it may require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. In some cases, it is desirable for the multiplexed systems to be compact in order to effectively utilize the light that is available from the analytical reaction and to be cost effective. In addition, it is desirable that the compact systems provide high tolerance to vibration, temperature uniformity, and reasonable instrument size and weight. It would therefore be desirable to provide analytical systems that have high multiplex for their desired analysis, and particularly for use in highly sensitive reaction analyses, and in many cases, to do so while providing a compact optical system that effectively mates an array of analytical reactions with an optical detector. The present invention meets these and a variety of other needs.

BRIEF SUMMARY OF THE INVENTION

In some aspects the invention comprises a detection system for measuring the emitted light from an array of patches of nanoscale regions comprising: a chip having an array of patches of nanoscale regions, each patch of nanoscale regions having an array of nanoscale regions; wherein light is emitted from the nanoscale regions from at least a first emitter and a second emitter, each emitting a different spectral range of light; an emitted light collection system comprising an array of compact lens trains (CLTs), each CLT corresponding to a patch of nanoscale regions, wherein each CLT comprises: a collimating lens for collimating light from the emission sources; a color separating element for spectrally separating light; and a focusing lens for focusing light from the color separating element; and a detector comprising an array of pixels onto which the focusing lens focuses light; whereby images of the nanoscale regions are focused onto the detector such that some pixels on the detector detect signal corresponding to the first spectral range, and some pixels on the detector detect signal corresponding to the second spectral range, thereby separately detecting light corresponding to the first emitter and the second emitter over time.

The nanoscale regions can comprise zero mode waveguides. The chip can comprise a waveguides which provide excitation light to the nanoscale regions. The detection system can comprise an array of microlenses below the nanoscale regions wherein each nanoscale region has a microlens.

The CLT can further comprise a rejection filter for selectively rejecting excitation light. Each patch of nanoscale regions can comprise 1,000 to 50,000 nanoscale regions.

The chip can be in contact with a fluid sample comprising at least a first fluorescent species and a second fluorescent species, wherein the first fluorescent species can act as a first emitter when within or proximal to a nanoscale region, and the second fluorescent species can act as a second emitter when within or proximal to a nanoscale region.

The first and second fluorescent species can comprise labeled nucleotide analogs. The array of CLT's can have from 9 to 400 CLTs. The array of CLT's can have from 25 to 100 CLTs.

The array of CLT's can comprise an array of plates, each plate comprising an array of optical elements. The array of CLTs can comprise a collimating lens plate comprising an array of collimating lenses, a color separating element plate comprising an array of color separating elements, and a focusing lens plate comprising an array of color separating elements. The collimating lens can comprise a gradient index (GRIN) lens. The collimating lens can comprise a gradient index (GRIN) lens and an aspheric lens.

The color separating element can comprise a grating, a prism, or a grating prism. The color separating element can comprise a dichroic filter that transmits light corresponding to the first emitter and reflects light corresponding to the second emitter.

The light from each nanoscale region can be dispersed in one direction across a set of pixels on the detector. Two or more sets of images of nanoscale regions can be formed on the detector, wherein one set of images is formed with light corresponding to the first emitter, and one set of images is formed with light corresponding to the second emitter.

The CLT can comprise a telecentric lens system. The CLT can comprise a non-telecentric lens system. The CLT can comprise a non-telecentric lens system, and the chip comprises an array of microlenses below the nano scale regions wherein each nanoscale region has a microlens. The CLT can further comprise a field flattening lens between the focusing lens and the detector.

In some embodiments the area taken up by a patch of nanoscale regions on the chip is within a factor of 3 of the area of the portion of the detector onto which the patch of nanoscale regions is focused. The distance between the chip and the detector can be less than two times the largest lateral dimension of the detector or the chip. The distance between the chip and the detector can be less than about 30 mm.

The detector can comprise a plurality of sensors. The plurality of sensors can comprise 2 to 9 sensors.

In some aspects the invention comprises a method for measuring the emitted light from an array of patches of nanoscale regions comprising: providing a chip having an array of patches of nanoscale regions, each patch of nanoscale regions having an array of nanoscale regions; wherein light is emitted from the nanoscale regions from at least a first emitter and a second emitter, each emitting a different spectral range of light; passing the emitted light through an emitted light collection system comprising an array of compact lens trains (CLTs), each CLT corresponding to a patch of nanoscale regions, wherein within each CLT: light from the emission sources is collimated with a collimating lens; the light is spectrally separated by a color separating element; and light from the color separating element is focused onto a detector with a focusing lens; and detecting light corresponding to the first emitter and second emitter over time on a detector comprising an array of pixels; whereby images of the nanoscale regions are focused onto the detector such that some pixels on the detector detect signal corresponding to the first spectral range, and some pixels on the detector detect signal corresponding to the second spectral range.

The nanoscale regions can comprise zero mode waveguides. The chip can comprise a waveguides which provide excitation light to the nanoscale regions. The chip can comprise an array of microlenses below the nanoscale regions wherein each nanoscale region has a microlens.

The CLT can further comprise a rejection filter for selectively rejecting excitation light. Each patch of nanoscale regions can comprise 1,000 to 100,000 nanoscale regions.

The chip can be in contact with a fluid sample comprising at least a first fluorescent species and a second fluorescent species, wherein the first fluorescent species can act as a first emitter when within or proximal to a nanoscale region, and the second fluorescent species can act as a second emitter when within or proximal to a nanoscale region. The first and second fluorescent species can comprise labeled nucleotide analogs. The array of CLT's can have from 9 to 400 CLTs. The array of CLT's can have from 25 to 100 CLTs. The array of CLT's can comprise an array of plates, each plate comprising an array of optical elements.

The array of CLTs can comprise a collimating lens plate comprising an array of collimating lenses, a color separating element plate comprising an array of color separating elements, and a focusing lens plate comprising an array of color separating elements. The collimating lens comprises a gradient index (GRIN) lens. The collimating lens can comprise a gradient index (GRIN) lens and an aspheric lens.

The color separating element can comprise a grating, a prism, or a grating prism. The color separating element can comprise a dichroic filter that transmits light corresponding to the first emitter and reflects light corresponding to the second emitter. The light from each nanoscale region can be dispersed in one direction across a set of pixels on the detector.

Two or more sets of images of nanoscale regions can be formed on the detector, wherein one set of images is formed with light corresponding to the first emitter, and one set of images is formed with light corresponding to the second emitter. The CLT can comprise a telecentric lens system. The CLT can comprise a non-telecentric lens system.

The CLT can comprise a non-telecentric lens system, and the chip comprises an array of microlenses below the nanoscale regions wherein each nanoscale region has a microlens. The CLT can further comprise a field flattening lens between the focusing lens and the detector. The detector can comprise a plurality of sensors. The plurality of sensors can comprise 2 to 9 sensors.

In some aspects the invention comprises an analysis system for measuring emitted fluorescent light from an array of patches of nanoscale regions comprising: (a) a holder for receiving a chip, the chip having an array of patches of nanoscale regions in contact with a reaction fluid, each patch of nanoscale regions having an array of nanoscale regions; wherein fluorescent light is emitted from the nanoscale regions from at least a first emitter and a second emitter, each emitting a different spectral range of light; (b) an illumination system providing excitation illumination to the nanoscale regions on the analysis chip, (c) an emitted light collection system comprising an array of compact lens trains (CLTs), each CLT corresponding to a patch of nanoscale regions, wherein each CLT comprises: (i) a collimating lens for collimating light from the emission sources; (ii) a color separating element for spectrally separating the light; and (iii) a focusing lens for focusing light from the color separating element; and (d) a detector comprising an array of pixels onto which the focusing lens focuses light; whereby images of the nanoscale regions are focused onto the detector such that some pixels on the detector detect signal corresponding to the first spectral range, and some pixels on the detector detect signal corresponding to the second spectral range, thereby separately detecting light corresponding to the first emitter and the second emitter over time.

The chip can comprise an array of waveguides that bring excitation light to the nanoscale regions. The illumination system can comprise a dichroic prism array. In some embodiments, the holder can be adjusted in three dimensions in order to align the chip. In some embodiments, the holder can be adjusted in six dimensions in order to align the chip.

The nanoscale regions can comprise zero mode waveguides. The chip can comprise a waveguides which provide excitation light to the nanoscale regions. The chip can comprise an array of microlenses below the nanoscale regions wherein each nanoscale region has a microlens.

The CLT can further comprise a rejection filter for selectively rejecting excitation light. Each patch of nanoscale regions comprises 1,000 to 50,000 nanoscale regions.

The chip can be in contact with a fluid sample comprising at least a first fluorescent species and a second fluorescent species, wherein the first fluorescent species can act as a first emitter when within or proximal to a nanoscale region, and the second fluorescent species can act as a second emitter when within or proximal to a nanoscale region.

The first and second fluorescent species can comprise labeled nucleotide analogs. The array of CLT's can have from 9 to 400 CLTs. The array of CLT's can have from 25 to 100 CLTs. The array of CLT's can comprise an array of plates, each plate comprising an array of optical elements.

The array of CLTs can comprise a collimating lens plate comprising an array of collimating lenses, a color separating element plate comprising an array of color separating elements, and a focusing lens plate comprising an array of color separating elements.

The collimating lens comprises a gradient index (GRIN) lens. The collimating lens can comprise a gradient index (GRIN) lens and an aspheric lens. The color separating element can comprise a grating, a prism, or a grating prism.

The color separating element can comprise a dichroic filter that transmits light corresponding to the first emitter and reflects light corresponding to the second emitter.

The light from each nanoscale region can be dispersed in one direction across a set of pixels on the detector.

Two or more sets of images of nanoscale regions can be formed on the detector, wherein one set of images is formed with light corresponding to the first emitter, and one set of images is formed with light corresponding to the second emitter. The CLT can comprise a telecentric lens system. The CLT can comprise a non-telecentric lens system. The CLT can comprise a non-telecentric lens system, and the chip comprises an array of microlenses below the nanoscale regions wherein each nanoscale region has a microlens. The CLT further can comprise a field flattening lens between the focusing lens and the detector.

The area taken up by a patch of nanoscale regions on the chip can be within a factor of 3 of the area of the portion of the detector onto which the patch of nanoscale regions is focused. The distance between the chip and the detector can be less than two times the largest lateral dimension of the detector or the chip. The distance between the chip and the detector can be less than about 30 mm.

The detector can comprise a plurality of sensors. The plurality of sensors can comprise 2 to 9 sensors.

In some aspects the invention comprises an illumination system for providing excitation illumination to an array of patches on a chip, wherein the patches emit fluorescent light, comprising: a two dimensional (x, y) array of dichroic prisms, each prism comprising a dichroic element that diverts illumination light up in the z dimension to a patch on a chip above it, and each dichroic element transmitting fluorescent light emitted by the patches, such light emitted light passing through each dichroic prism.

The illumination system can comprise an array of prisms with N rows by M columns, further comprising a column of M beam splitting elements along an edge of the dichroic element, wherein when illumination light is sent down the column of beam splitting elements, each of the M beam splitting elements diverts a portion of the illumination light into a row of N dichroic elements, and each of the N dichroic elements in the row diverts a portion of light to a patch above it.

The number of dichroic prisms can be from about 10 to about 1,000. The number of dichroic prisms can be from about 50 to about 200.

In some aspects the invention comprises a method for providing excitation illumination to an array of patches on a chip, wherein the patches emit fluorescent light, comprising: providing, below the chip, a two dimensional (x, y) array of dichroic prisms, each prism comprising a dichroic element, sending excitation illumination light into the array of dichroic prisms such that each dichroic prism diverts illumination light up in the z dimension to a patch on the chip above it, stimulating fluorescent emission from the patches, whereby the emitted light passes through the dichroic prisms.

The array of dichroic prisms can be an array of prisms with N rows by M columns, further comprising a column of M beam splitting elements along an edge of the dichroic element, wherein illumination light is sent down the column of beam splitting elements, and each of the M beam splitting elements diverts a portion of the illumination light into a row of N dichroic elements, and each of the N dichroic elements in the row diverts a portion of light to a patch above it.

The number of dichroic prisms can be from about 10 to about 1,000. The number of dichroic prisms can be from about 50 to about 200.

BRIEF DESCRIPTION OF THE DRAWINGS

FIG. 7A shows a micro-lens toward the middle of a chip directing light down the center of the lenses in the CLT. FIG. 7B shows a micro-lens toward the edge of the chip that directs light at a target range of angles.

FIG. 11A illustrates the incorporation of nucleotides by an immobilized polymerase complex, and FIG. 11B illustrates optical output from such analytical reactions at nanoscale regions.

FIG. 12A utilizes sensor BAE 2521 from Fairchild. FIG. 12B uses a pair of BAE 2020 sensors from Fairchild butted side. FIG. 12C uses the a Dynamax 0174 sensor.

DETAILED DESCRIPTION OF THE INVENTION

General

Figure 1:
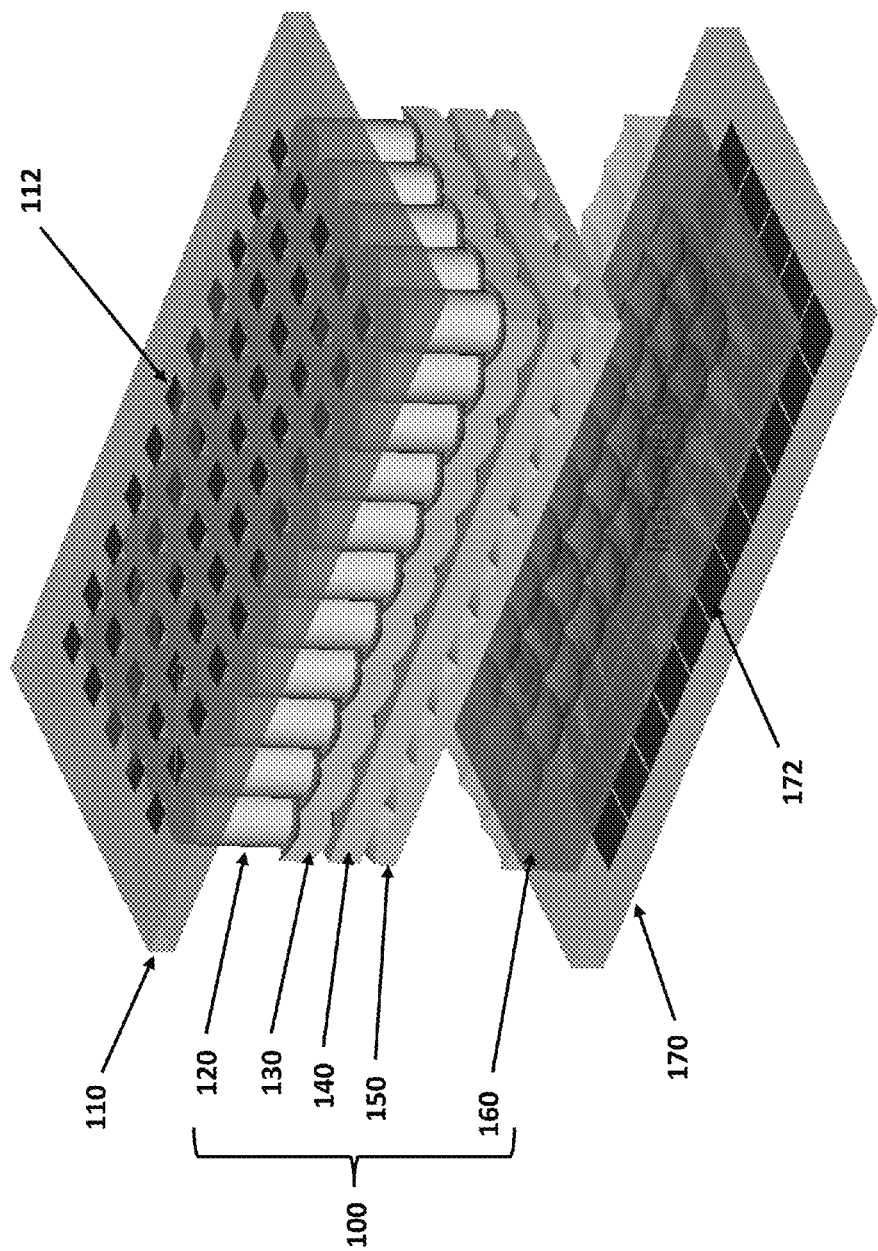
FIG. 1 shows a device of the invention comprising a chip, a compact lens train array, and a detector.

The analytical devices, systems, and methods of the invention utilize arrays of nanoscale reaction regions which are observed simultaneously, providing multiplexed optical analytical systems that can be used in a wide variety of applications. Such applications include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the systems of the invention are of broader application.

One object of the invention is to carry out and optically analyze hundreds of thousands to millions of analytical reactions simultaneously, where each reaction is occurring within a nanoscale region on a substrate. The optical analysis is typically carried out using one or more optical detector having millions of pixels in aggregate. In order to observe reactions occurring in each of the nanoscale regions, the emitted light from each of the regions must reliably be directed to a corresponding portion of the detector. In addition to optically observing the reactions occurring in the nanoscale regions, it is also typically desired to observe emissions corresponding to two or more spectral regions at one time, e.g. observing light from two or more fluorescent labels. One important application is real time single molecule sequencing, which is described in more detail below, in which signals corresponding to different labels are used to distinguish which base has been added to a growing nucleotide strand. For sequencing, it is typically desired to observe whether one of four bases is added to a growing strand which can be accomplished with different spectral signals from e.g. two, three, or four spectrally distinct labels. One approach to such multiplex analysis has been to send all of the light emitted from an array of nanoscale regions through a single lens train, e.g. through a single objective lens. These single lens train approaches can lead to a large diameter and a long optical path length resulting in losses in optical signal, and to a large, expensive optics system. The current invention provides a compact system for the collection of emitted light from arrays of nanoscale regions and for separating the emitted light into at least two spectral regions for which the size of the collection optics is much smaller than for a conventional single-objective system.

The analytical devices of the invention use an array of nanoscale regions (a chip) that has discrete patches, also called islands, of nanoscale regions. The chip mates with a collection device comprising an array of compact lens trains (CLTs) where each of the CLTs corresponds to a single patch of nanoscale regions. Each CLT collects the emitted light from a patch on the chip, collimates the light, performs color separation on the collimated emitted light, then focuses the separated light onto a portion of pixels on the detector below the CLT. The CLTs are produced such that they are abutting their neighbor CLTs so as to effectively utilize the pixels on the detector. Each patch on the chip together with the CLT and the image of the patch on the detector together may be called a "tile" and a sufficient number of tiles will cover the detector. For example, each CLT can collect and direct the light from a patch of 5,000 to 20,000 nanoscale regions. If there 100 CLTs, then from 500,000 to 2 million nanoscale regions can be imaged onto the detector. If the detector has, for example 5 million to 20 million pixels, then for the case of 1 million nanoscale regions, there can be between 5 pixels to 20 pixels for each nanoscale region, and if the images from each nanoscale region is divided into two colors for two spectrally distinct labels, then 2.5 pixels to 10 pixels per label are available on the detector for each label in the nanoscale region. The numbers described here are provided to illustrate how the current invention can be used to measure a million reactions simultaneously on a detector. These numbers do not represent the limits of these values, which are described more fully herein.

The collection arrays of the invention provide the flexibility and scalability to utilize available sensors regardless of their size, aspect ratio, and even the presence of pixel gaps such as might arise in butted arrangements. The nanoscale optical regions or ZMWs are grouped into patches or islands with finite gaps in between, and each island is imaged (typically with magnification) through a dedicated lens train onto a sensor below. We use the term "tile" to refer to each individual collection array element and the image it produces on the sensor. Each tile comprises the series of lens train, a color separation unit (grating, prism, or dichroic splitter). This tiling enables us to adapt to the size and aspect ratio of available sensors. No matter their size or aspect ratio, we can arrange a tiling format to fill the sensor. The gaps between islands provide room for waveguide routing or other chip infrastructure without impacting multiplex. The gaps can also be used for multiple sets of ZMWs to be read sequentially, i.e., multiple looks. Where the nanoscale regions are illuminated by waveguides, the use of islands reduces the length of illumination waveguides along which illumination light must propagate, thus enabling the use of higher loss waveguides and lowerer total instrument laser power. In some cases, a 7×13=91 lens trains and would support simultaneous observation of about 700 k nanoscale regions.

FIG. 1 provides an example of an analytical detection system of the invention. For the example shown, the number CLTs, and therefore the number of nanoscale patches is 55 in an array of 5 by 11. This is provided for illustration, and the number of CLTs could be any practicable number, for example from about 10 to about 1,000 or from about 50 to about 200. An analysis chip 110 has a number of patches of nanoscale regions 112. Each of the patches of nanoscale regions typically has thousands of nanoscale regions, for example between 1,000 and 20,000. The nanoscale regions can be, for example, zero mode waveguides. The nanoscale regions will typically be in contact with a reaction solution comprising components of the analytical reaction including labeled species. In the case of a sequencing reaction, for example, a single template-polymerase enzyme complex is in each nanoscale region, and the incorporation of nucleotides to a growing strand complementary to the template is determined by observing the residence time of labeled nucleotide analogs in the reaction solution.

The chip having the nanoscale regions will typically be on a transparent substrate or on a substrate having transparent regions, allowing for light from emitted from the nanoscale regions on the top surface of the chip to pass down through the transparent regions to the lens train below. The chip will also typically have an array of optical elements such as micromirrors or microlenses that focus or re-direct the light emitted from the nanoscale regions. There is typically one micromirror or microlens per nanoscale region.

The emitted light is thus send down through the CLT array 100 to the detector 170. The detector 170 is commonly a single die, but may also be a small number of abutted sensors, or may comprise a mosaic of sensors. The mapping of islands to the detector, or detector mosaic, may be many to one, one to one, or one to many, depending on the details of the island and sensor die apertures and shapes, and the magnification of the CLT. The CLT array comprises an array of 55 lens trains, each lens train imaging one patch of nanoscale apertures onto a portion of the detector. The CLT array is made up of a series of plates, each with an array of 55 optical elements. The plates are combined to form the CLT array. The CLT array can have any suitable lens element including elements for collection, focusing, color separation, blocking, selective rejection, redirecting, reflecting, polarization, or image flattening. For example, as shown in FIG. 1, each CLT has a gradient index (GRIN) lens 120 and an aspheric lens 130 for collimation of the light from the chip, a color separating element 140 such as a prism or grating, an aspheric lens 150 for focusing the light from the color separator onto the detector, and a flattening lens 160 for ensuring focus across the detector 170 typically having a substantially flat surface. Where fluorescent labels are used, the CLT will also typically have a laser rejection filter for selective rejection of the illumination light, for example, a dichroic filter between the aspheric lens and the color separation element.

The detector 170 has a number of regions 172, each typically comprising multiple pixels. In FIG. 1, square patches of nanoscale regions 112 are imaged onto square regions 172 of the detector. The shape of the patches and images can be any suitable shape, and the image can have a different shape than the patch of nanoscale regions. Rectangular patches can be used to more fully utilize the available detector by matching its length to width aspect ratio. In FIG. 1, the image of the nanoscale region is larger than the dimensions of the nanoscale region, i.e. the magnification is greater than 1. Having a magnification of greater than 1 can be advantageous as having the light entering the CLT nearer the center of the CLT and away from the edge of the CLT can be advantageous for utilization of the lens, and magnifying the patch to the edges of the CLT can provide for better utilization of the pixels on the detector. Magnification of the patch also opens up regions on the chip between the patches for other uses such as routing of illumination light through waveguides or for fluid delivery systems or for any other use. Although these regions are opened on the chip, there is no loss of multiplex because all of the pixels on the sensor are still fully utilized. In some cases the magnification of each CLT is greater than 1, for example from 1.2 to about 5, or from about 1.5 to about 3.

In one example a chip with dimensions of about 14 mm by 14 mm has an 8 by 8 array of patches, each with about 7,200 zero mode waveguides. The patches are about 0.9 mm by 0.9 mm. The thickness of the CLT array is about 7 mm. The images from the patches are magnified to fill about a 1.8 mm by 1.8 mmm square on the detector, thus each of the patches is magnified by a factor of 2. The detector is about 14.4 mm by 14.4 mm, thus, in this example, while each patch is magnified by a factor of 2, the overall area of the chip and the detector are similar.

The detector can have, for example 2,800 by 2,800 pixels that are 5 micron by 5 micron. In some embodiments, the nanoscale regions are arranged in rows and columns in which the spacing on one dimension is greater than the spacing in the other. For example, the spacing between the nanoscale regions in rows is about 7.5 microns, and the spacing between nanoscale regions in columns is about 15 microns. For this approach, a prism, grating, or grating prism (sometimes referred to as a grism) is used to spread out the colors in the column direction, for example in the case where there are two spectrally distinct labels. Using spreading of spectra across a detector to monitor multiple labels simultaneously is described, for example in U.S. Pat. No. 7,805,081 which is incorporated herein by reference for all purposes. This embodiment can provide a multiplex of greater than 460,000.

In an analytical system or instrument, the CLT array and the detector are typically assembled and kept together as part of the instrument. The chip 110 is typically a consumable that is exchanged after each experiment or after a few experiments. The chip can be a single or multiple use chip. The instrument receives electrical signals from the detector chip for processing to monitor the analytical reaction.

In some cases, the analytical systems are fluorescent systems, which further include illumination components for providing illumination (excitation) light for the fluorophores. In some cases, the chip includes waveguides that accept illumination light from the instrument and direct it to the nanoscale regions as described for example in U.S. Pat. No. 7,820,983, U.S. Pat. No. 7,834,329, U.S. Pat. No. 7,838,847, U.S. Pat. No. 8,053,742, and U.S. Pat. No. 8,207,509 which are incorporated herein by reference for all purposes. In some cases, illumination light is provided to the chip from a separate light pipe element or can be provided from above the chip and re-directed to the nanoscale regions. In some cases, illumination is provided by a dichroic prism array as described herein.

Figure 2:
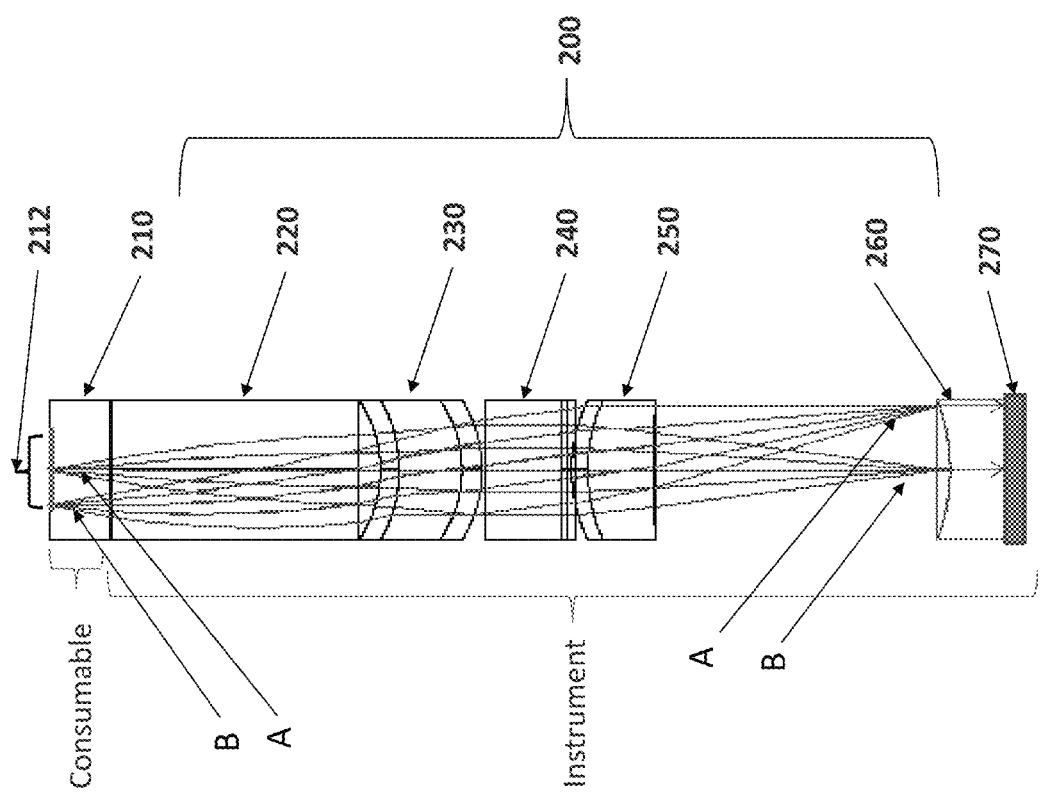
FIG. 2 illustrates how emitted light from nanoscale regions on a chip pass through the lens train and are focused onto a detector.

FIG. 2 shows an exemplary CLT 200 and the corresponding portion of the chip 210, and detector 270. The figure illustrates an approach to directing emitted light rays A and B from the patch of nanoscale regions 212 to the detector 270. The CLT 200 has a gradient index (GRIN) lens 220, an aspheric collimating lens 230, which can be a plastic lens, a grating prism 240 for spectral separation of the emitted light, an aspheric focusing lens 250, which can be a plastic lens, and a flattening lens 260 which helps focus the light onto the flat detector 270. For fluorescent systems, the CLT will also have an illumination light rejection filter, typically disposed before or after color separation element, e.g. grating prism 240. The rejection filter may reside in other places along the lens path. It may even reside on multiple surfaces along the lens path in order to increase total blocking. The illumination light rejection filter may also include the function of enforcing a sharp bandpass on the signal, which can aid in increasing multiplex for a given detector by reducing spectral crosstalk. One aspect of the invention is to provide lens systems which minimize or eliminate vignetting in the lens system in order to utilize a high fraction of pixels on the detector. As shown in FIG. 2, emitted light rays A from a nanoscale region from the center of the patch of nanoscale regions 212 are focused onto the center of the detector portion 270, and emitted light rays B from a nanoscale region near the left edge of the patch of nanoscale apertures 212 are focused onto the right edge of the detector portion 270. This approach provides for a high utilization of the pixels on the detector. As shown in FIG. 2, the chip portion having the nanoscale regions is a consumable, while the CLT and detector are part of the instrument. Here, the chip 210 is shown in contact with the CLT 200. In other cases the chip is held a distance away from the CLT. Typically, in addition to the patches of nanoscale regions, e.g. zero mode waveguides, the chip has an array of optical elements such as microlenses or micromirrors that direct the light from each of the nanoscale regions into the CLT.

As described herein, while this figure shows a single CLT, which is part of an array of CLTs that are typically packed next to each other in order to effectively utilize the area of the detector. The CLTs of the invention are typically produced as an array that is formed by combining plates, each plate having an array of elements. For example, in some cases, the array of CLTs comprises an array of GRIN lenses 220, an array of aspheric lenses 230, an array of grating prisms 240, an array of illumination light rejection filters, an array of aspheric lenses 250, and an array of flattening lenses 260. These arrays are assembled to produce the CLT array which is mated with the detector. The spacing, tilt, and lateral positioning of the CLT array with respect to the detector may be adjusted in order to maximize optical performance, particularly image sharpness across the detector. In some cases, each plate comprises an array of one type of element. In some cases, an array of more than one optical element is included in a plate.

Figure 3:
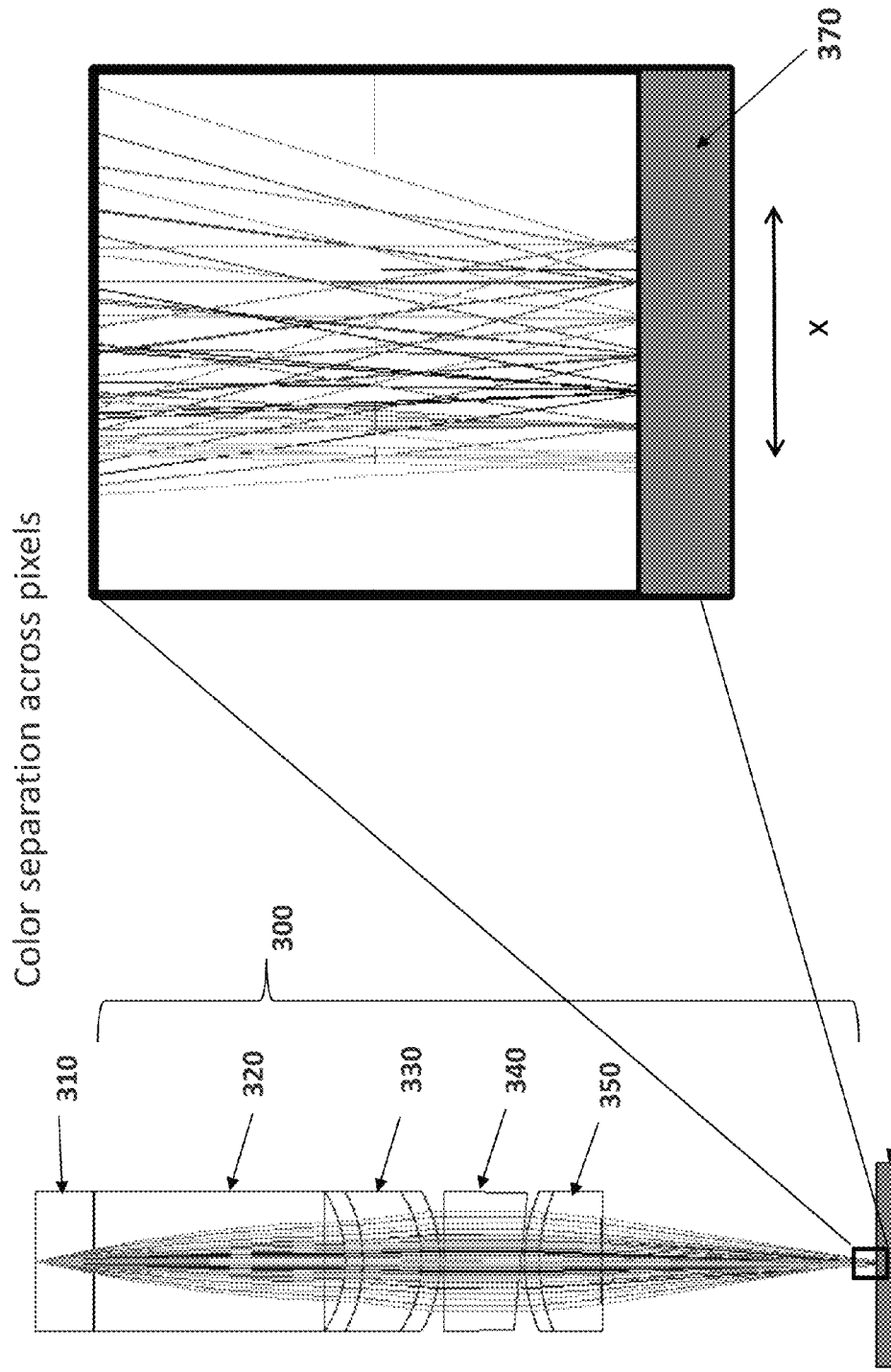
FIG. 3A illustrates how a compact lens train with a color separation element can spread the spectrum of emitted light across pixels on a detector.
FIG. 3B magnifies a portion of FIG. 3A to illustrate how the colors are separated in space at the detector.

FIG. 3 shows an approach of the invention for monitoring multiple labels simultaneously with the analytical devices and systems of the invention. FIG. 3A shows how the CLT 300 accepts emitted light from nanoscale region on chip 310 which passes through GRIN lens 320, aspheric lens 330, grating prism 340, aspheric lens 350, and focuses the light onto detector 370. The grating prism 340 causes spectral dispersion of the light so that different portions of the spectrum will fall on different sets of pixels on the detector. FIG. 3B shows a magnification of a region where the light from the nanoscale region impinges on the detector 370 illustrating how the light of different wavelengths is spread out across a dimension, arbitrarily illustrated here as the x dimension. The light can be spread across 2, 3, 4, 5, 6, 7, 8, 9, 10 or more pixels in the x direction of the detector. Spreading out the light makes each of the pixels sensitive to a different portion of the light spectrum, allowing for the differentiation of 2, 3, 4, or more spectrally distinct labels.

Figure 4:
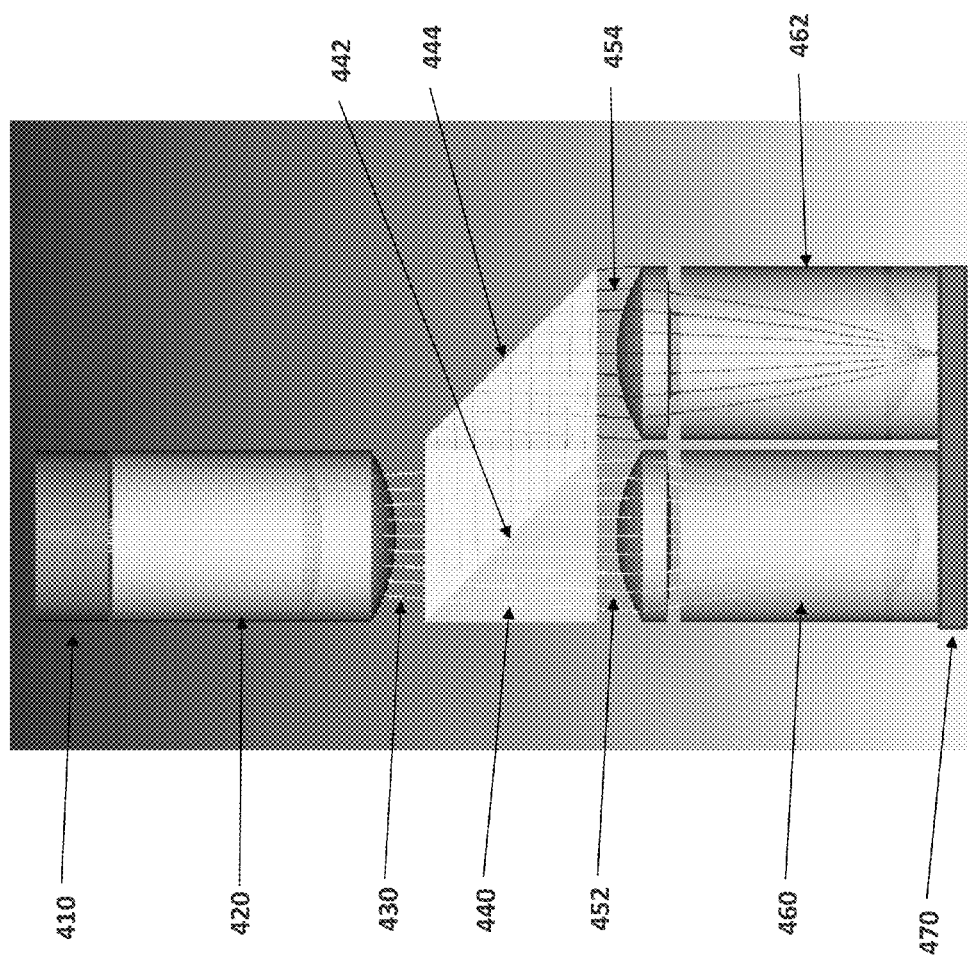
FIG. 4 shows an alternative approach to color separation with a compact lens train.

In some cases, color separation can be carried out in the CLT using one or more dichroic mirrors to selectively transmit and reflect portions of the emitted light. FIG. 4 shows an example in which the CLT separates the emitted light into two spectral regions, each spectral region imaged onto a different portion of the detector. FIG. 4 represents a single CLT which is part of an array of CLTs between chip 410 and Detector 470. Light is emitted from a nanoscale region within a patch of nanoscale regions on chip 410. The emitted light enters collimating lens or lenses 420. The light 430 that emerges from the collimating lens or lenses 420 enters color separation element 440. Color separation element 440 has a dichroic element 442 that allows light from a first spectral range to pass, and reflecting light in a second spectral range. The light from the first spectral range 452 passes through the color separation element into focusing lens train 460 which focuses the light in the first spectral range onto a first region of the detector 470, the light from the second spectral region 454 is reflected off of mirror 444 down into focusing lens train 462 which focuses the light in the second spectral region onto a second portion of the detector 470. Light in the first spectral region corresponds to a first label in the nanoscale region, and light in the second spectral region corresponds to a second label in the nanoscale region. This color separation approach also allows for simultaneously monitoring emission from two, three, four, or more different spectral labels. FIG. 4 shows a CLT for separation of two spectral regions. By using more dichroic elements and mirrors, the same approach can be used to monitor more than two spectral regions, for example, three or four spectral regions.

The CLT arrays of the invention provide a number of benefits. The relatively small field of view for the lenses in the CLT allow for a simpler lens train than is required where one lens train is used, allowing for equal or better optical performance with fewer lens elements. By dividing the light from the array of emitters, the noise is divided and compartmentalized. This provides benefits in controlling noise for example from autofluorescence and crosstalk. The CLTs also provide for the efficient use of real-estate on the chip.

The CLT arrays allow for routing and splitting closer to the nanoscale optical element (e.g. ZMW). The CLT arrays allow for the flexible use of sensors, both for optimizing the use of the pixels on a given sensor, and for tiling multiple sensors. Each CLT can be produced to send the light to a portion of the detector below it, and the CLTs can be arranged next to one another in a manner that provides a high utilization of pixels on the detector.

The detector that is used in the instant invention can be a single sensor or detector, or can be made of a number of sensors or detectors tiled together to form the detector. For example, it can be desirable to be able to analyze a large number, for example 1 million to 5 million nanoscale optical regions simultaneously, but it may be difficult to obtain a sensor or detector with the required number of pixels to do this effectively. In this case, the sensors or detectors can be butted together to form a detector under the CLT to provide the desired number of pixels. In some cases, the detector is made up of two sensors butted together on one side. In some cases, the detector has 3, 4, 5, 6, 7, 8, 9, 10, 11, 12, 13, 14, 15, 16, 17, 18, 19, 20, 21 or more detectors in a mosaic. In some cases the detector has 2 to 12 sensors. Typically each sensor has greater than one million pixels, in some cases each sensor has greater than 5 million pixels. The use of multiple sensors put together as a mosaic detector allows for utilizing the best and most cost effective commercially available sensors to produce the analytical devices of the invention.

Arrays of Optical Elements

Figure 5:
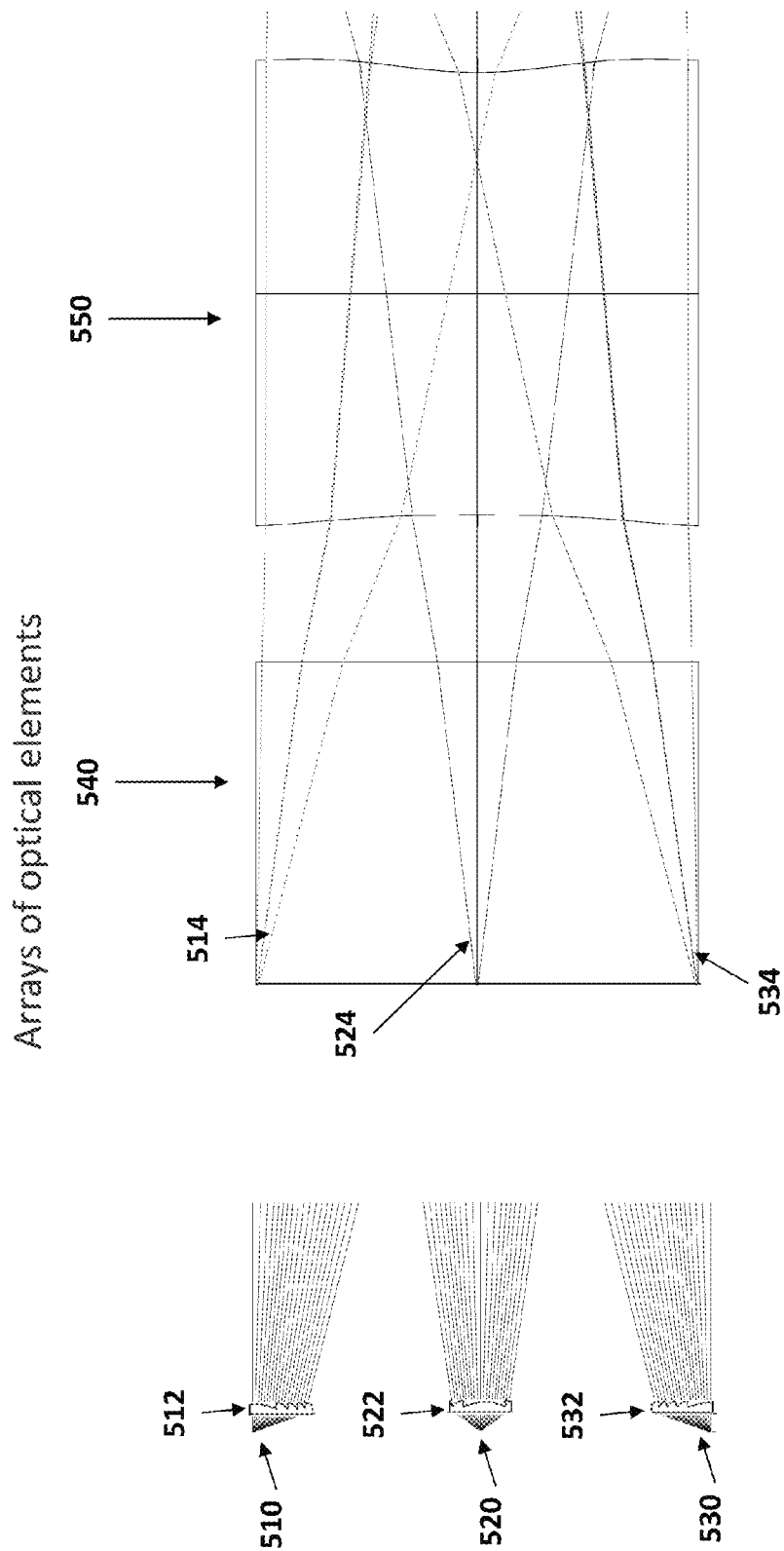
FIG. 5A illustrates a chip having an array of optical elements with different characteristics across the chip.
FIG. 5B shows how light rays from nanoscale regions across the chip are transmitted by a portion of a compact lens train, with the lenses near the edge of the chip directing the light at different angles than lenses near the center of the chip.

The chips of the invention typically include an array of optical elements, for example, one optical element for each nanoscale region with in a patch of nanoscale regions. The optical elements are typically lenses, for example Fresnel lenses, and in some cases can comprise micromirrors. Having one optical element for each nanoscale region allows for improving the collection of the emitted light from the nanoscale regions. In one aspect the optical elements can redirect the emitted light in order to prevent crosstalk between the regions and to allow for a lower NA collection system, which is generally advantageous for imaging performance, cost, size, and transmission of the collection system optics. However, there is a lower limit to the NA of the collection system, below which the diffraction limited spots of light limits the resolvable points on the detector. As an approximation, the optical PSF should be smaller than the larger of the detector pixel size, or the PSF of the sensor (e.g., due to charge diffusion). For example, a detector with 6.5 um square pixels, or a sensor PSF of 6.5 micron scale, would require an optical system with NA on the detector not less than about 0.1 for light of wavelength ~630 nm. The light on the object side (next to the chip) would then need to have NA not less than 0.1 times the CLT magnification, or typically 0.26. In some cases the characteristics of the optical elements is varied across the patch of nanoscale regions in order to control where the image of the nanoscale region is focused onto the detector. FIG. 5 shows an example of this redirection by lenses 512, 522, and 532. In FIG. 5A light is emitted from nanoscale region 520 near the center of a patch of nanoscale regions, and from nanoscale regions 510 and 530 near the edges of the patch of nanoscale regions. The emitted light is emitted, for example, close to isotropically. Lenses 512, 522, and 532 re-direct the emitted light from the nanoscale regions. Lens 522, near the center of the patch, is axially symmetric, directing the light straight down the optic axis of the lens system. Lenses 512 and 532 direct the light at an angle with respect to the optic axis of the lens system. FIG. 5B shows how the light rays form these lenses pass into the CLT. Light rays 524 correspond to light rays from lens 522 directed down the optic axis of the lens system. It can be seen that the light rays leave the chip 540, and enter the CLT 550 on axis. In contrast, light rays 514 and 534 from lenses 512 and 532 respectively exit the chip 540, and enter the CLT at an angle with respect to the optic axis of the lens train of the CLT. This approach can improve the utilization of the lens, and can be used to reduce or eliminate vignetting. It can also provide good optical performance for patches with a relatively large area with respect to the area of the CLT. In FIG. 5, the nanoscale regions at the edges of the patch are close to the outside edge of the CLT, where the ratio of the area of the patch of nanoscale regions to the entrance to the CLT is approximately 1:1. In some cases, the approach allows for the ratio of area of the patch to the CLT opening to be about 0.99:1, 0.98:1, 0.97:1, 0.96:5, 0.95:1, 0.9:1, 0.8:1, 0.7:1, 0.6:1, or 0.5:1 or from about 0.99:1 to 0.5:1.

Slowly varying microlenses non-telecentrically across a defined ZMW field of view offer a good opportunity to aim the flux collected from each ZMW through a free-space optic of size comparable to the nanoscale region (e.g. zero mode waveguide) field of view. This permits fabrication of scalable free space optic consistent with a chip having high duty cycle of nanoscale apertures.

A nanoscale aperture or ZMW that is on axis is typically telecentric, that is, the principal ray is parallel to the optical axis of the free space collection system. See for example, FIG. 5, nanoscale region 520. Where all ZMWs in a patch are projected telecentrically, there can be substantial (e.g. 50%) vignetting for the ZMWs at the edge of a patch of ZMWs. In addition, the vignetted light can contribute to background in adjacent tiles, and can form a second ZMW image resulting in localized, periodic, cross-talk.

Figure 6:
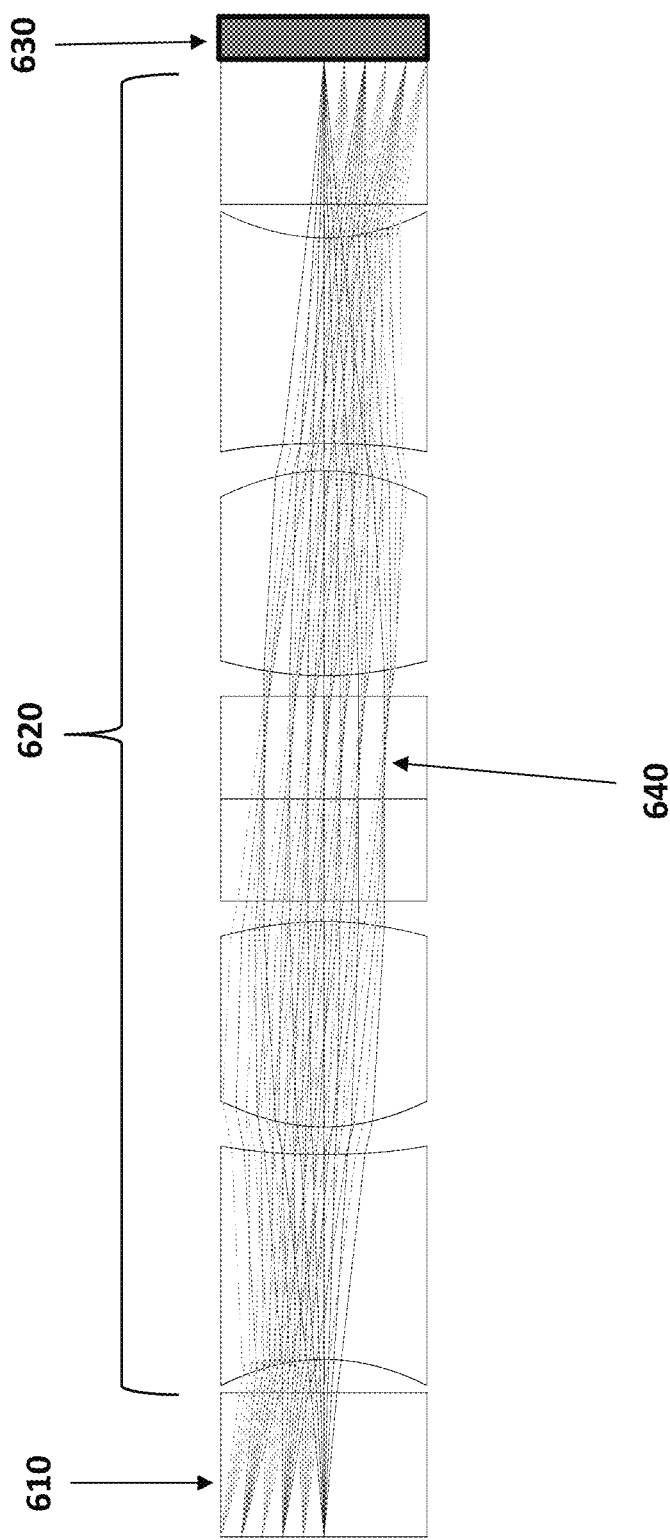
FIG. 6 shows a non-telecentric optical system, where there is a finite NA collected from each nanoscale region that is transmitted efficiently through all of the free space optics.

FIG. 6 shows a non-telecentric optical system, where there is a finite NA collected from each ZMW that is transmitted efficiently through all of the free space optics. This arrangement preserves signal strength, and avoids detrimental optical background and periodic crosstalk. The property of non-telecentricity is to form an aperture stop at some point other than infinity. In a magnification equals about 1 system, which is particularly useful for high density scalable free-space collection optics, that aperture stop will be near the center of a symmetric system. Moderate departures of symmetry can be accommodated. In FIG. 6, the principal rays cross the axis near 640 near the center of the optical train, inside a central optic (for example, a color spreading GRISM). This plane corresponds approximately to the aperture stop.

This is accomplished by controllably aiming principle rays towards this stop by slowly varying the angle with respect to the optical axis. This can be done, for example, by a slowly varying prescription to an optic element associated with each nanoscale region or ZMW on the chip. This can be considered as the combination of a space invariant micro-lens (to achieve a target reduced NA), plus a micro-prism that varies in prism power slowly across each patch. This approach can be implemented with two binary optic elements, or alternatively, to have a single lens designed with an oversized aperture, and use a slowly varying decenter in the aperture of the lens that is used at each ZMW.

Figure 7:
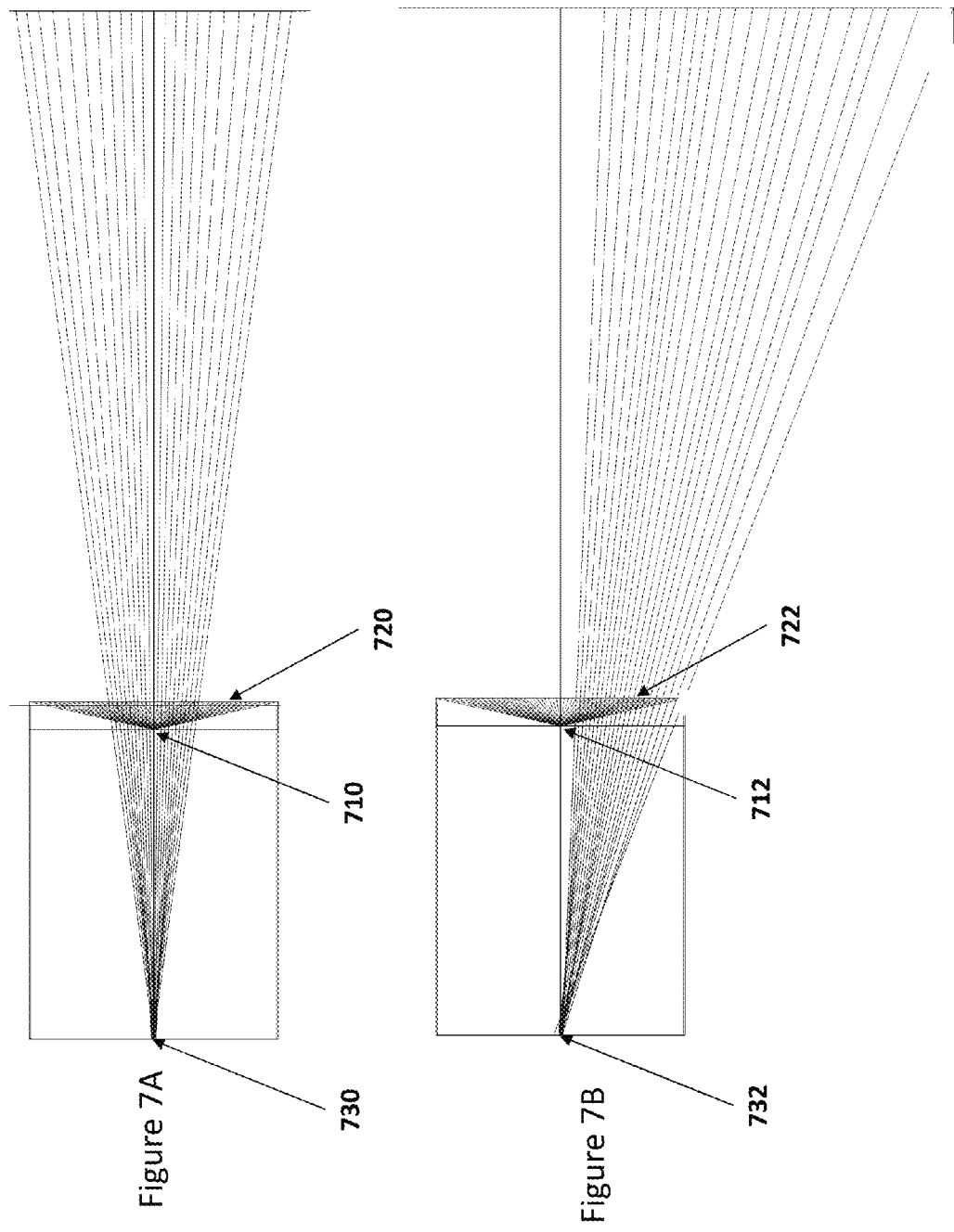
FIGS. 7A-7B show how lenses in different portions of the chip direct the light differently into the CLT.

FIG. 7A shows a point source 710 close to a diffractive binary optic micro lens 720, and a more distant, virtual image point source 730 corresponding to the lower NA emission from the micro lens. The aperture is centered on the lens function, leading to a telecentric output consistent with a nanoscale region on axis in a given tile. FIG. 7B shows an off-center aperture which directs the collected flux to a target range of angles. A point source 712 is close to a diffractive binary optic micro lens 722. The lens produces a more distant, virtual image point source 732. The configuration of FIG. 7B is used, for example, near the edges of the patches of nanoscale regions to direct the light more effectively into the CLT. The choice of the virtual image is important for maximizing the NA collected from a nanoscale region.

In some cases, the choice of the virtual image point is subject to a finite minimum fabrication feature in lithography of producing the binary lens. For example, in some cases the minimum lithography feature size is about 150 nm. A virtual image can require smaller deviation of the rays collected to create the lower NA re-imaged by the instrument. That smaller deviation angle can require a grating vector with a smaller magnitude, and hence for any given NA collected a larger period in the grating fabrication. Comparing a virtual image to an equivalent real image, the NA collected can increase to 1.25 from 0.85 for an instrument NA of 0.2, a substantial increase in potential collection efficiency (e.g., potentially up to a 2× signal increase, and a decrease in fluoresced signal light that could contribute to background noise). The limitation of the fabrication minimum feature size can also play a role in the non-telecentric function. With relatively small impact to collection efficiency (compared to the >2× signal increase), the aperture can be moved off-center to collect up to NA 1.42 (close to the maximum of NA 1.457 for silica) on one edge while still maintaining a minimum feature size of >150 nm. (see FIG. 7B). The degrees of freedom of a micro-lens at each nanoscale region can be used to vary the NA emitted across the tile, and also to provide a field curvature correction.

The micro lens can be a binary optic, and can be diffractive, refractive, or a combination of diffractive and refractive. The microlens may also be more than a single layer, e.g., a combination of discrete lens and prism in close axis proximity is possible. In some cases the lens is not binary or stepped, and in some cases can be continuous. The microlens aperture can be apodized to control the far field pattern. The optics of the CLT can be designed for different NA emitted. The number of optical elements in the CLT can be chosen to obtain the desired performance. In some cases, as in the design illustrated here, the design is corrected for axial chromatic aberration. The CLT lens design may be asymmetric. The symmetry illustrated herein can be helpful for controlling distortion, and achieving pixel matched optical systems. The design of FIG. 7 utilizes color spreading for identifying multiple labels. Other label discrimination methods than color spreading can also be incorporated.

In some cases the magnification of the system is greater than 1, which means that the size of the image of a patch of nanoscale regions on the detector is greater than the size of the patch. For example a linear dimension in an image of a patch on the detector is from about 1.2 times to about 10 times the corresponding linear dimension in the patch. In some cases, a linear dimension in an image of a patch on the detector is from about 1.3 times to about 5 times the corresponding linear dimension in the patch. In some cases, a linear dimension in an image of a patch on the detector is from about 1.5 times to about 3 times the corresponding linear dimension in the patch.

Figure 8:
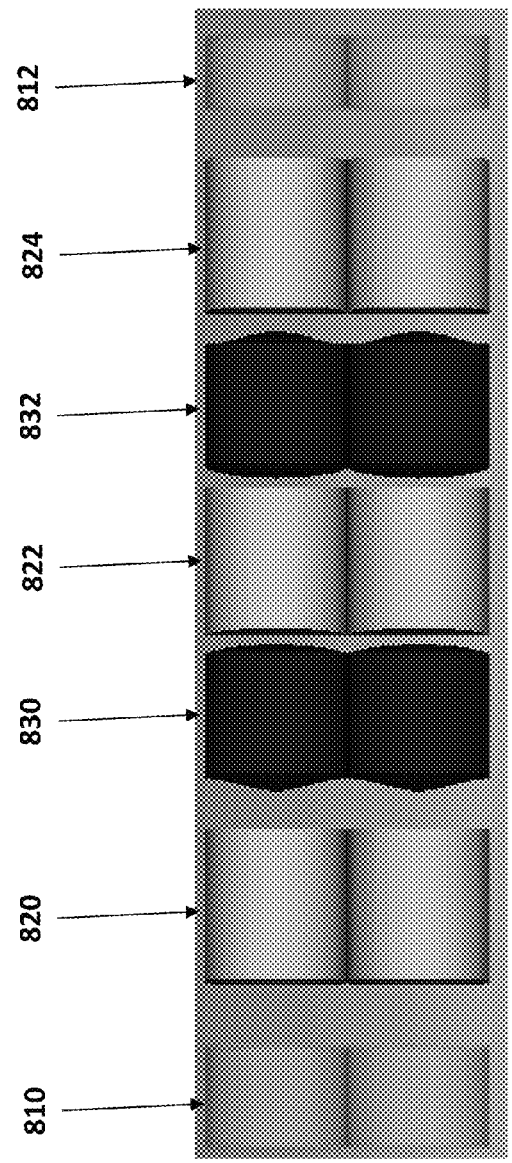
FIG. 8 shows an exemplary layout for a CLT array with a magnification around 1.

In some cases, the magnification of the system is about 1, meaning that the size of the image of a patch of nanoscale regions on the detector substantially the same as the size of the patch. FIG. 8 shows an exemplary lens train (showing two CLTs in an array of CLTs). For the lens trains in FIG. 8 there is no gradient index lens or field flattener. Any suitable material can be used to provide the optical elements. For example, in some cases, elements 810 and 812 are made from SiO2, elements 820, 822, and 824 are made from a polymer such as Ultem™ (e.g. Ultem™ 1010), and elements 830 and 832 are made from a polymer such as Zeonex™ (e.g. Zeonex™ E48R). It is generally desirable that the lens material have a relatively high refractive index. It can also be desirable for the lens materials to have low birefringence, low water absorption, and/or high service temperature. E48R and Ultem are a favorable combination for an achromatized optical system, owing to the substantial difference in dispersion, the relatively high refractive indices among polymer choices for crown and flint roles, and the relatively close match in CTE of Zeonex and Ultem which improves the stability of a sub-assembly.

In some aspects, the invention provides a detection system for measuring the emitted light from an array of patches of nanoscale regions. The emitted light is indicative of a chemical or biochemical reaction occurring at or near (proximate to) the nanoscale regions. The emitted light can be, for example, fluorescent light from labeled compounds in a solution that is in contact with the nanoscale regions. In some cases, the nanoscale patches have immobilized biomolecules such as enzymes or binding molecules such as antibodies. The nanoscale regions typically have a small number of such biomolecules, for example, having only a single active enzyme or active binding molecule. The enzyme can be, for example a nucleic acid polymerase, and the labeled compounds can be fluorescently labeled nucleotide analogs. The analytical system can be used to determine the presence over time of labeled components in the solution. Light emanating from the nanoscale region is indicative of the presence of the labeled compound at or near the biomolecule within the nanoscale region. Light is emitted from the nanoscale regions from at least a first emitter and a second emitter, each emitting a different spectral range of light. In some cases, there are three, four or more differently labeled compounds, where each of the two, three, four, or more labels emits a different range of wavelengths. The systems of the invention are produced to monitor the emissions of each of these two, three, four, or more labels over time in each of an array of nanoscale regions.

The detection system has a chip that has an array of patches of nanoscale regions, each patch of nanoscale regions having an array of nanoscale regions. The chip is typically a consumable element, used for one or a few experiments, and then replaced. The remaining optical and electrical components are part of an permanent instrument to which the consumable chip is reversibly mated. They nanoscale regions are disposed on the chip to be accessible to a fluid solution comprising the reaction mixture. In some cases, there is a single fluid reservoir above the chip. In some cases, there are fluidic conduits that bring different fluids to different portions of the chip. Typically the fluid is introduced into the top of the chip, and emitted light is emitted out of the bottom of the chip. Thus, the chip is typically made from a transparent material such as silica, or has transparent portions below the nanoscale regions in order to allow emitted light to travel down to the detection optics. The patches of nanoscale regions are arranged on the chip so that, for example, each patch corresponds to one lens train in an array of lens trains. The patches will typically have from 1,000 to 10,000 nanoscale regions, but can have any suitable number of regions.

The chip will typically have an array of optical elements such as microlenses or micromirrors below the nanoscale regions, where the light from each nanoscale region is sent through a microlens that re-directs the light from that nanoscale region down into the CLT below it. Having one microlens or micromirror allows for sending the light from each nanoscale region within a tighter set of angles, reducing the amount of crosstalk, and increasing the amount of light that is effectively passed into the CLT. In some cases, as described in more detail herein, the characteristic of each microlens or micromirror will be varied across the patch of nanoscale regions in order to allow the CLT to most effectively direct the light to the detector.

A patch on the chip corresponds to a compact lens trains (CLT) below the chip. An array of patches corresponds to an array of compact lens trains below the chip. Each CLT processes the light from one patch of nanoscale regions. The CLT receives the light from the chip, separates the light into spectral regions, and focuses the light corresponding to the spectral regions onto a portion of a detector below the CLT.

Typically, each CLT comprises at least: a collimating lens for collimating light from the emission sources; a color separating element for spectrally separating light from the collimating lens; and a focusing lens for focusing light from the color separating element. The color separation can involve spreading out the spectra across the detector, for example with a prism, or separating portions of the spectrum to be focused on different portions of the detector, for example using dichroic elements and mirrors.

The spectrally separated light is focused by the CLTs onto the detector. The detector has an array of pixels such that different pixels on the detector detect signal corresponding to different spectral range for each of the nanoscale regions. This allows the detector to monitor signal from the two, three, four or more different labels for each of the nanoscale regions over time.

The use of this analysis system including an array of CLT's provides a compact instrument. The CLTs are designed to effectively utilize the pixels on the detector. For example, the light from the patches is magnified such that the images of the nanoscale region extend to the edge of each CLT, providing little or no dead space (wasted pixels) between the CLTs.

The nanoscale regions of the inventions are small regions, typically with lateral dimensions less than 300 nanometers in which analytical reactions can be observed. The analytical instruments of the invention can be used to observe small number of molecules, and are specifically directed at observing reactions at a single molecule level. The nanoscale regions of the invention can be zero mode waveguides which are described in more detail herein and in documents incorporated by reference. As ZMWs are the prototypical nanoscale region, where a description of a device or instrument is presented as using an array of ZMWs, it is to be understood that other suitable nanoscale regions may also be used. The devices and systems of the inventions are typically directed at simultaneously monitoring analytical reactions at 100s of thousands to millions of nanoscale regions. The total number of nanoscale regions on a chip can be from 100,000 to 10 million, or from 200,000 to 1 million. The hundreds of thousands of nanoscale regions are divided into groups or patches in the devices of the invention, and the images of each group of nanoscale regions is processed individually through its own CLT in an array of CLTs. Typically a patch of nanoscale regions will include from about 1000 to about 100,000 nanoscale regions or from about 1,000 to about 10,000 nanoscale regions. The number of patches typically is the same as the number of CLTs, and the number of CLTs that is used can be chosen to enhance the performance of the system. The number of CLTs can be, for example, from about 10 to about 1,000, or from about 25 to about 500, or about 30 to about 200. For example the chip can have 100 patches, each with 5,000 nanoscale regions for an instrument with 100 CLTs for a multiplex of 500,000. The chip can have 100 patches, each with 10,000 nanoscale regions, for a multiplex of 1 million.

The nanoscale regions are in fluid contact with a fluid comprising the components of an analytical reaction. The analytical reaction is carried out in a manner such that a luminescent event in the nanoscale region is indicative of the occurrence of the analytical reaction. For example, the fluid can have compounds that diffuse in and out of the nanoscale regions, and a luminescent signal (e.g. a fluorescent signal) is enhanced when the compounds participate in a reaction within the nanoscale region. For example, a single active biomolecule can be immobilized within the nanoscale region, and a component that may react with that biomolecule can be in solution. In some cases, the single active biomolecule is an enzyme or protein having a binding interaction. A substrate for the enzyme or binding compound for the protein can be labeled such that its interaction with the enzyme or with the binding protein is observable. In some cases the interaction can create an observable luminescent species, in some cases there is a longer residence time of a luminescent species where a reaction or interaction occurs, and in some cases there is an interaction such as a FRET interaction between the single biomolecule and the compound in solution that produces an observable luminescent signal. The luminescence can be chemiluminescence fluorescence. The instruments and systems of the instant invention can be used to observe an analytical reaction over time where the analytical reaction has two, three, four or more luminescent signals, each with a different spectral range. An analytical reaction for which the instruments and devices of the invention are particularly useful is single molecule real time sequencing, which is described in more detail herein.

The CLTs comprise free-space optical elements which can be configured as desired to improve optical performance. The CLT typically has at least a collimation lens or lens assembly for collimating the light emitted from the patches of nanoscale regions, a color separation element for separating two, three, four, or more colors, and a focusing lens or lens assembly for focusing the light from the color separation component onto the detector. The color separation element can comprise, for example, a dispersive element such as a prism or grating with spreads out the spectrum onto different portions of the detector, or can comprise a color separation system such as one or more dichroic elements that split the spectrum into components that are directed to different parts of the detector.

In addition to these elements, the CLT will also often have a field flattening lens or lens assembly for allowing focusing of the images across a patch onto the typically flat detector. The devices and systems of the invention are often used with fluorescent systems, in which case the CLT will typically include an illumination light rejection component. The illumination light rejection component improves the signal to noise by making sure that stray illumination light does not make its way to the detector. The illumination light rejection component can be reflective, absorptive, or a combination of reflective and absorptive. In some cases an absorptive illumination light rejection component is preferred to prevent reflecting illumination light back toward the chip resulting in interference.

One of the objectives of the devices and systems of the inventions is to provide a compact illumination system, and at the same time minimize or eliminate vignetting. The array of CLTs provides images onto a detector which typically has an uninterrupted array of pixels. It is desired that the images from the CLTs effectively utilize the pixels on the detector. These goals are accomplished in several ways in the instant invention in ways that can in some cases by combined. In some cases, vignetting is minimized or eliminated by using patches that have dimensions that are smaller than the dimensions of the images of the patches on the detector. This allows for the lens system of the CLT to effectively image the patch onto the detector by having the patch enter the center portion of the lens, avoiding the edges where vignetting may become an issue. In some cases, the vignetting is minimized by having microlenses, e.g. Fresnel lenses which vary in focusing properties across the chip, sending light into the CLT at varying angles in a manner that optimizes the use of the detector, and avoids vignetting. These approaches can be combined.

Plastic optical elements are well known in the art. Such elements are available, for example through Thorlabs™, and Edmund™ Optics. Descriptions of such lenses are found in Handbook of Plastic Optics, Stefan Baumer, editor. Wiley-VCH; 2nd edition (Apr. 5, 2010), The Design of Plastic Optical Systems, Michael P. Schaub; SPIE Press (2009) and in U.S. Pat. No. 7,262,925 which are incorporated by reference herein in their entirety for all purposes. Arrayed lenses have been described, for example by Nalux™, and Dmetrix™. Array lenses are described in U.S. Pat. No. 6,842,290 which is incorporated herein by reference for all purposes.

Dispersive Color Separation

In some cases, color separation is achieved by dispersing the emitted wavelengths in space, for example along one axis. Typically, the optical signals emanating from the source derive from reactive chemical species, where the reaction of such species either produces, extinguishes, increases, decreases, or otherwise alters the characteristic of the optical signals. Such reactive species include chromogenic or chromophoric reactants, e.g., that produce a shift in the transmissivity of the material to light of one or more wavelengths, i.e., changing color upon reaction. Reactant species that emit light, either with the use of an activating light source (fluorescent or fluorogenic) or without such an excitation source (luminescent) are preferred for use in the methods of the invention. Further, in the context of the invention, such reactive species are most preferably contained in fluid solutions and are provided as reaction mixtures where the different optical signals result from the substrates, the products, or combinations of the two.

In some aspects, the different optical signals to be detected are comprised of light of differing wavelengths, e.g., emitted by different fluorophores where such emissions have different wavelength spectra, or transmitted by different chromophores where such transmissions are at different wavelength spectra. In such cases, the two or more different optical signals are spatially separated, e.g., through the use of a beam splitter in combination with one or more dichroic filters, or through the use of a prism or optical grating, and the different signals are directed to different locations on an optical detector or detector array. In alternate aspects, the different optical signals may differ in other characteristics, such as their relative polarity, their modulation phase or frequency, or the like, provided that they may be spatially separated and directed to different regions on a detector or detector array, e.g., through the use of polarizing or demodulation filters. Examples of biochemical assays based upon such differing characteristics are described in, e.g., U.S. Pat.

No. 6,699,655, which discloses monitoring reaction progress by detecting of the relative polarity of fluorescent reactants and products (typically in combination with a polarization affecting agent) when excited with polarized light.

The methods of spatial separation and/or direction of different optical signals to different locations on an optical detector or detector array is generally dependent upon the characteristic(s) of the different optical signals that is/are to be the basis of differential detection. For example, where the different optical signals differ in their wavelength, separation and direction can be accomplished through the use of optical filters and/or prisms that selectively transmit or redirect light of differing wavelengths in different manners and/or to different degrees. For example, a collected signal that comprises two different wavelengths of light emanating from a confined source may be split into two beams, e.g., through the use of a dichroic filter to remove the other signal component, then passed through a barrier filter, thereby allowing only a portion of the overall signal to be directed to the optical detector or detector array. In accordance with the invention, however, a simpler optical train is employed to separate optical signals and direct them to different locations on a detector or detector array, or in some cases, to multiple different detectors or detector arrays. In particular, a wedge prism or optical grating may be employed to achieve this result. The use of such prisms or diffraction gratings provides simplicity to the optical train of the overall system and results in a more transmissive light path as compared to more complex optical systems. Additionally, in contrast to the use of cut-off filters, e.g., dichroics, the entire spectrum of signal, or at least a more selectively filtered portion of the signal, less, e.g., the reflective losses of the prism, may be directed to the detector or detector array. As a result, there is a greater amount of signal available for detection, manipulation and deconvolution.

Although the color separation element shown in this application is often shown as a single prism or grating, it will be appreciated that in some cases, it may be desirable to use more than one prism or grating. Suitable color separation elements include, for example, those described in U.S. Patent Publication 2008/0080059, which is incorporated herein by reference for all purposes. In particular, in some cases, the spatial separation of different signals resulting from the dispersion profile of a given prism may not achieve a desired spatial separation. For example, in cases of high density of detector elements in a detector array, it may be desirable to provide for regularly or linearly spaced signal components. However, the dispersion profiles of given prism may not be linear, e.g., the resulting transmitted signals are not equally spatially separated. However, where detection is facilitated by ensuring all signals have similar separation relative to each other, e.g., in using CCDs for detecting dense collections of signals, it may be advantageous to combine prisms with dissimilar dispersion profiles to provide a near linear separation profile for each of the signals being detected. Likewise, in certain cases, detection of different signals may be optimized by providing greater separation between two or more signal components than a linear separation might afford. In such cases, the tunability of two or more prisms allows for this increased flexibility of the system. In addition to the use of additional prisms or gratings, it will be appreciated that tuning of the system may be accomplished by rotating the prism or other dispersive optical element, e.g., around the optical axis of the optical system and also perpendicular to the direction of color separation, to adjust the degree of dispersion. Thus, in system embodiments, it may be useful to provide one or more of the prisms in a configuration that is capable of being readily rotated about the axis.

ZMW Array

The nanoscale regions of the invention can comprise zero mode waveguides (ZMWs). For example, large numbers of zero mode waveguides can be provided arrayed in rows and columns on the substrate. Within the various ZMWs are provided reactants of interest for a given analysis. For example, in the context of nucleic acid sequencing by synthesis, a sequencing complex that includes a template nucleic acid sequence, a complementary primer sequence, a nucleic acid polymerase enzyme, and a reaction mixture of nucleotides or nucleotide analogs required for primer extension are provided with the ZMW. ZMW arrays can be fabricated at ultra-high density, providing anywhere from 1000 ZMWs per $cm^2$, to 1,000,000 ZMWs per $cm^2$, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

Multiplex Approaches

The present invention provides methods, systems and components for monitoring increased numbers of arrayed complexes on substrates. By way of example, U.S. patent application Ser. No. 12/151,979, filed May 9, 2008, and PCT/US2008/05953, incorporated herein by reference for all purposes, describes methods of analyzing large numbers of arrayed reaction regions, e.g., nucleic acid sequencing complexes, using multiplex optics that direct targeted illumination spots to and collect optical signals from discrete reaction regions.

Thus, while the systems of the invention may be used to provide a multiplex analysis of 10, 100, 1000, 5000 or the like discrete reaction regions on a substrate, in particularly preferred aspects, the invention will be employed to provide multiplex analysis of greater than 5000 discrete reaction regions, greater than 10,000 discrete reaction regions, greater than 20,000 discrete reaction regions, greater than 50,000 discrete reaction regions, and even greater than 100,000 discrete reaction regions, and up to 1,000,000 or more discrete reaction regions. In addition to the sheer number of reaction regions analyzable by the systems of the invention, it will be appreciated that in some cases, such reaction regions can be disposed at higher densities than previously employed, through the various advantages provided by the invention. For example, discrete reaction regions can be provided and observed at high densities without excessive interference or other problematic issues. Such densities can be, e.g., 1000, 10,000, 100,000, 1,000, 000, 10,000,000, or more reaction regions per $cm^2$. For example, up to 16 e9 observations volumes per square centimeter could be visualized in a square array, slightly more for a hexagonal close-packed array. The diffraction limit could be exceeded through the use of near-field optics, leading to a limitation governed only by the physical size of the confinements, which can be as small as 50 nm in size. Separated by 100 nm in a square array, this leads to a density of 1e10 per square centimeter.

Further, such multiplex analysis will be substantially simultaneous with respect to the number of regions being monitored. By "substantially simultaneous", is meant that within the timeframe of 1 to 5 (preferably 1 to 2) camera frames, the requisite number of regions has been analyzed. For purposes of the systems of the invention, a camera frame is typically captured from about every 1 ms to about every 10 ms (or frame rates of from about 100 Hz to about 1000 Hz), so that to be within the range of a substantially simultaneous analysis, analysis of such multiplex regions shall occur within a time span of from about 1 ms to about 10 ms. As a result, a system that provides the desired multiplex analysis, e.g., observing multiple locations at least once each within a window of from 1 ms to about 10 ms, will be said to be substantially simultaneous, even if the analyses are carried out at two distinct time points within that window.

In some cases, slower frame rates may be employed, which would increase the time period in which two events may occur while still appearing to be substantially simultaneous from the perspective of the camera. For example frame rates of 10 Hz to 100 Hz, 10 Hz to 50 Hz, 10 Hz to 20 Hz, e.g., approximately 15 Hz, may be employed. As will be appreciated, sampling rates that occur on the millisecond range may be viewed as being substantially simultaneous, e.g., from 1 ms to about 500 ms, 10 ms to about 100 ms, or the like.

Arrays of Nanoscale Regions Having Micromirror or Microlens Structures

The chips of the invention with arrays of nanoscale regions such as zero mode waveguides typically also have arrays of optical components on the chip for directing the emitted light from the chips onto the array of CLTs. These arrays of optical components are typically either micromirrors or microlenses, or in some cases a combination of both. These elements are described, for example, in U.S. Pat. No. 8,247,216 and U.S. Patent Publication 2013/0023039 which are incorporated herein by reference for all purposes. Typically there is one such optical component for each nanoscale region, but other ratios of nanoscale region to optical component can be used.

This optical approach provides addition of focusing optics that serve to minimize optical cross-talk among reaction regions, and also allow provides flexibility for the choice of collection lenses in the CLT's. By decreasing cross-talk potential, one improves the ability to close pack reaction regions. Simultaneously, by moving to a higher field of view objective, one can expand the area in which such regions are disposed. In addition to lowering cross-talk, the focusing optics of the invention can also increase the amount of light that is detected by redirecting light into a detector that would otherwise not be detected by the detector without redirection. By redirecting the light, lenses in the CLT's can be used which, for example collect the same amount of light as without redirection, but have a lower numerical aperture, allowing, for example, a larger field of view. In the context of methods contemplated in this invention, having a large field of view can be important, for example, for allowing the simultaneous observation of tens of thousands of luminescing or fluorescing regions at once. Alternatively, by directing the light, the same numerical aperture can be used, while collecting more light. As described in more detail below, the focusing optics of the invention can also provide for increased levels of illumination by directing illumination light into a reaction region on an array, such as an array of zero-mode waveguides.

Micromirror Arrays

In some aspects of the invention, micromirror arrays are provided where there is one micromirror per nanoscale region or zero mode waveguide. These can be an array of shaped micromirrors wherein each micromirror is associated with a nanoscale region, and in particular an array of shaped micromirrors that is incorporated into the same substrate that comprises the optical confinements.

In particular, the conical or parabolic mirrors are typically comprised of a reflective material, such as a metal layer, e.g., aluminum, silver, gold, chrome, or the like, manufactured into the underlying substrate to provide the mirror surfaces.

Fluorescent signals emitted from the reactions within the nanoscale regions are redirected or focused by a mirror such as a parabolic or conical mirror increasing the efficiency with which such signals are collected. As shown here, for example omni-directional emitted light coming into the reaction regions on the substrate is redirected such that it is more readily detected. In some cases, as illustrated here, the light can be at least partially collimated. In addition, for each reaction region or ZMW, the mirror structure reduces or eliminates inter-ZMW cross-talk within the substrate itself. In addition to the reduction in cross-talk, it will be appreciated that the enhanced collection efficiency resulting from redirection or focusing of the emitted light also increases the sensitivity of the system.

Alternative configurations may also be adopted for the devices incorporating these conical mirrors. For example, a zero mode waveguide core region may be extended into the underlying substrate. Although the mirrors described herein are referred to as "conical" or as "parabolic" mirrors, it will be understood that such integrated reflective focusing optics components will be characterized by their ability to provide a reflective component within the substrate that enhances the detection of light by redirecting the light emitted from the reaction region through the substrate, irrespective of its precise shape. In some cases, the light emitted from the reaction region is at least partially collimated. The shaped mirrors of the invention will thus redirect light from an optical confinement on the substrate to a detector, or to an optical element that is part of an optical train bringing light from the substrate to a detector. The focusing mirrors may comprise shapes other than parabolic structures, such as conical mirror configurations, staged conical mirror configurations, truncated conical mirror configurations, partial parabolic mirror configurations, trapezoidal mirror configurations, pyramidal mirror configurations, and the like, provided such structures redirect the light, for example to enhance the detection of light emanating from or through the reaction region into the substrate, for example by partial collimation. In many cases, the mirrors will have a cylindrical symmetry. The shape of the mirror can be a prismatoid, for example, a pyramid, wedge, prism, antiprism, cupola, or frusta thereof. Where the mirror has multiple sides, such as where it comprises a pyramid or a frusta of a pyramid, the mirror can have any suitable number of sides. For example, where the mirror comprises a pyramid, the pyramid can have 3, 4, 5, 6, 7, 8, 9, 10, 11, 12, or more sides.

The shaped mirrors of the invention are generally micromirrors, meaning that the mirrors are small, generally having dimensions on the order of microns or tens of microns. In some cases the term microreflector is also used to refer to a micromirror. The mirrors can have a cross-sectional dimension from about 0.1 micron to about 100 microns, about 1 micron to about 50 microns, or about 2 microns to about 20 microns. While the mirrors of the invention have dimensions on the order of microns to tens of microns, in some cases, the shaped mirrors of the invention can be larger, for example from about 100 microns to about 1 mm or greater.

Further, although described in terms of providing a reflective material such as a metal layer within the substrate itself, it will be appreciated that other reflective configurations may be likewise employed without the use of a metal layer. For example, structures may be comprised of materials of differing refractive indices to provide for a reflective interface that performs the same function as the metal layers described elsewhere herein. For example, light that is traveling from a region of one refractive index across an interface into a region of a lower refractive index will generally be completely internally reflected if the angle of incidence of the light is greater than a give value (the critical angle). In this manner, reflective structures of the invention may be created without the use of a reflective layer by appropriately adjusting the refractive indices of the materials on either side of the shape.

In some cases, the shaped reflective structures of the invention comprise conical reflectors. The efficiencies in a conical reflector scheme show substantial improvements over non-reflector substrates both in theoretical models and experimentally. In some cases, conical structures are useful as they can be readily formed by a variety of processes. For example, the tapering of the walls can be controlled by controlling the geometry of the resist, and by the lithography conditions. The resist geometry can be controlled, for example, by controlling the focus/exposure conditions of the resist to control the topology of the resist, or by gray-scale lithography. The shape can also be controlled by controlling the etching conditions, for example, controlling the amount of surface passivation or by gray-scale etching. The conical mirror substrates of the invention generally comprise a truncated cone structure. The walls in the truncated cone section of the conical mirror substrates can be straight, or can include some curvature. The reflective surface of the shaped substrate can be provided, for example, by coating the protrusion with a reflective layer, by filling the region between protrusions with reflective material, or by using a lower refractive index medium outside of the protrusion to encourage internal reflection.

The micromirror arrays can be fabricated at a high density as described above for ZMW arrays. The density of micromirrors associated with reactive regions can be, for example, anywhere from 1000 ZMWs per $cm^2$, to 1,000,000 ZMWs per $cm^2$, or more. At any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate using the micromirror arrays described herein.

The zero mode waveguides are typically formed on a transparent substrate or on a layer of transparent material on an opaque, e.g. a silicon substrate, which can comprise inorganic materials, organic materials, or composite materials with both organic and inorganic materials. The transparent material is typically a rigid material which can keep the reactive regions in fixed positions during observation. Silica based materials, such fused silica are preferred materials. The transparent substrate may also comprise inorganic oxide materials and glasses. The transparent substrate material may be a heterogeneous material, such as a material having multiple layers. In some cases, for example, the transparent substrate may comprise a dielectric stack. Transparent polymeric materials can also be used. It is typically desired that the transparent material exhibit low levels of autofluorecence. Suitable transparent polymers comprise, for example, methacrylate polymers such as PMMA, polycarbonates, cyclic olefin polymers, sytrenic polymers, fluorine-containing polymers, polyesters, polyetherketones, polyethersulfones, polyimides or mixtures thereof.

The cladding layer is an opaque or reflective material. The cladding layer can be a metal such as aluminum, copper, gold, silver, chromium, titanium or mixtures thereof. In some embodiments, the reflective layer and the cladding layer comprise the same material.

Micromirrors or microlenses can be combined with zero mode waveguides to improve the efficiency of collection of the light from reactive regions on the substrate over the collection efficiencies which would be obtained without the mirror structures. The collection efficiency of an optical system is typically influenced by the numeric aperture of the collection system. The micromirrors or microlenses can improve the amount of light collected by a detection system having a given numeric aperture, e.g. a numeric aperture of 0.5, by greater than about 10%, 20%, 30%, 40%, 50%, 75%, 90%, 2 times, 3 times, 5 times, 10 times or more than the amount of light collected without the micromirrors. The numerical aperture of the detection system can be, for example, from 0.1 to 0.9. In some cases the numerical aperture is between about 0.2 and 0.5.

Micromirror and microlens structures can also increase the level of illumination of the reaction regions from an illumination source. For example, the level of illumination can be increased by greater than 20%, 30%, 40%, 50%, 75%, 90%, 2 times, 3 times, 5 times, 10 times or more than the level of illumination without the micromirrors or microlenses.

Fabrication of Micromirror Arrays

The micromirror arrays of the invention can be produced by a variety of methods. One aspect of the production of the arrays is the production of an array of structures such as protrusions on a transparent substrate. The array of structures can be produced by molding, stamping, embossing, machining, etching, or other suitable methods.

One preferred approach to producing the micromirror arrays of the present invention involves the use of microfabrication methods such as semiconductor or MEMS processing methods, which have been highly developed for the production, for example, of integrated circuits. Similar processes have been used to create MEMS (micro electromechanical systems) for a variety of applications including inkjet printers, accelerometers, pressure transducers, and displays (such as the digital micromirror displays (DMDs)). Microfabrication methods can be applied to a large substrate such as a wafer, which can later be diced into many devices, allowing for the production of many devices at one time. An aspect of the invention is the use of these processes for producing a micromirror array in a transparent substrate, such as a glass, e.g. fused silica. The methods of the invention apply resist processes, such as photoresists to define structural elements on the transparent substrate or other layers. Etching processes are used to produce three-dimensional structures including the reactive region and the micromirror structure. Deposition processes are used to add layers onto the substrate. Other semiconductor processes such as ashing, polishing, release, and liftoff are also employed to create the micromirror structures of the invention as described in more detail below.

The transparent substrate can be any suitable rigid transparent material. The transparent material can comprise, for example, an inorganic oxide material such as silica. A preferred material is fused silica.

One aspect of the invention is a process for producing substrates comprising arrays of reactive regions associated with incorporated micromirror structures by a method comprising the steps of: a) providing a transparent substrate having a top surface; b) patterning and etching the transparent substrate to form an array of protrusions having tops and sides; c) depositing a cladding material such that the tops of the protrusions comprise a cladding; d) forming an array of apertures through the cladding such that the top of each protrusion comprises an aperture; and e) depositing a reflective deposition material such that the sides of the each protrusions comprise a reflective layer; whereby the array of protrusions comprise an array of micromirrors, and the aperture at the top of each protrusion comprises a zero-mode waveguide. The process involves the production of both reactive regions and micromirror structures. One set of processes described herein in greater detail involves first producing the reaction regions, for example, as an array of apertures, and subsequently producing the micromirror structures. Another set of processes involves first producing micromirror structures on the transparent substrate and subsequently producing the reactive regions.

In order to produce the arrays of the invention it can be useful to combine different processes for the different features having different dimensional requirements. For example, the processes of the current invention may use a 193 nm lithography process for producing the reactive regions and I-line lithography for producing the micromirror structures. This is not a typical production process as it can require sending the substrate from one fabrication facility to another fabrication facility in the middle of the process.

Integrated Lens Arrays

As with integrated parabolic mirrors, lens arrays may be fabricated using a variety of conventional technologies, including for example semiconductor fabrication processes, micromolding of polymeric materials, and the like. For example, as with components of the fabrication process for the integrated mirrors, described above, etching processes such as reactive ion etching may be employed to produce such lens arrays. Alternatively, as noted above, variable ion implantation processes may be employed to vary refractive index of substrate components to define lenses with an existing substrate. As will also be appreciated, additional optical elements that provide for improved collection of light from the reaction regions may be fabricated into the substrate as well. For example, the foregoing ion-implantation processes may be used to define diffraction gratings for each different reaction region directly in the substrate.

In alternative aspects, conical or parabolic mirrors are replaced with (or in some cases, augmented with) lens arrays that at least partially collimate or focus the fluorescent signals to and/or from the substrate.

The lens array may be integrated into the underlying transparent substrate. Alternatively, the lens array may be separately fabricated and joined to the underlying substrate to provide the same or similar results. Although illustrated as a single layer of lenses disposed at the back surface of the array, it will be appreciated that the lens array may be comprised of multiple lens layers that each address different regions on the substrate, or combined to provide a desired optical functionality at a given region on the substrate. Additionally, although illustrated as lenses protruding from the back surface of the transparent substrate, in some cases, the lenses may be integrated within the transparent substrate. For example, lenses may be fabricated into the underlying substrate at the appropriate locations by providing variations in the index of refraction of the substrate in such locations. Discrete lenses can be embedded in the substrate using micromachining techniques to provide binary index of refraction, as in conventional lens fabrication. Additionally, by creating a gradient of refractive index at selected portions of the substrate, these portions of the substrate can function as lenses. Alteration of the refractive index of the substrate, e.g., a glass substrate, can be accomplished a number of ways, including, for example, ion implantation methods. In addition to lenses or lens arrays, diffractive gratings or other optical functionalities could likewise be fabricated into the underlying substrate.

Because the signals from the substrate are at least partially collimated by the focusing optics, the need for narrow field of view, high numerical aperture objectives is reduced, and larger field of view, lower NA objectives may be employed, which generally imparts cost and availability advantages to the overall system, as less stringently manufactured objectives may be used. In addition, the exotic materials used to manufacture higher power objectives can give rise to increased photoluminescence of the objective itself, when exposed to excitation radiation.

In addition, because lower power objectives are employed, greater spacing can be provided between the objective and the substrate than is generally provided when employing high numerical aperture objectives. This additional spacing permits the insertion of additional optical components, e.g., appropriate dichroic(s), between the substrate and the collection objective. In at least one exemplary embodiment, provision of a dichroic between the substrate and the objective allows the separation of the illumination light from the collection objective (and other collection optics components. By further separating the excitation path from the detection path, and particularly by providing a collection objective that does not see excitation light, one can completely eliminate autofluorescence or photoluminescence in the collection path that results from passage of excitation illumination through that objective.

Illumination

Where the emitted light from the nanoscale regions is fluorescent light, illumination of the nanoscale regions must be provided to provide excitation of the fluorophores. The illumination is typically provided by one or more lasers, but in some cases light emitting diodes or other suitable light sources can be employed. The light from the source is directed to the nanoscale regions using an illumination system. Typically, the illumination is provided from below the nanoscale region. Light is provided from below in particular where the nanoscale regions comprise zero mode waveguides. Illumination from below is also useful in that, as described herein, the reaction solution is often above the nanoscale region, and illumination from below allows for illumination without having to pass the light through the reaction solution.

The illumination can be provided to the chip using planar or channel waveguides in the chip. Such waveguides are described, for example in U.S. Pat. No. 7,820,983, U.S. Pat. No. 7,834,329, U.S. Pat. No. 7,838,847, U.S. Pat. No. 8,053,742, U.S. Pat. No. 8,207,509, US 2012/0014837, US 2012/0021525, and US 2012/0019828 which are incorporated herein by reference for all purposes.

In some cases, the illumination of the nanoscale regions on the chip can be carried out using multiple illumination sources in combination with one or multiple diffractive elements to illuminate large numbers of discrete reaction areas. In such cases, two, three, four, five, ten or more laser beams may be directed through one or more diffractive optical elements to generate large numbers of illumination spots on a substrate.

In illuminating large numbers of discrete regions on a substrate, e.g., using a diffractive optical element to provide discrete beams, ensuring adequate power is delivered to large numbers of illuminated areas typically requires increases in the power applied to the system. For ultra-high multiplex systems, individual illumination sources for doing this are not commercially viable, due to cost and availability.

For example, in certain exemplary applications, single illumination source beams are divided into beamlets that provide ~5 µW/µm². Achieving the same illumination power for 80,000 discrete spots would suggest a single illumination beam of ~500 mW.

In addition to laser issues, diffractive optical elements typically generate beam patterns that that have reasonable beam uniformity over relatively small fields of view. However, where one desires to expand the field of view, the non-uniformity of the illumination pattern can become excessive for certain applications. Thus, in expanding multiplex illumination, e.g., an order of magnitude or greater, one would expect substantial variation in illumination intensity across the illumination spots.

Accordingly, in some cases illumination sources and/or source beams are directed through the diffractive element or diffractive elements in order to provide ultra-high multiplex illumination with readily available, lower power illumination sources, and greater uniformity across the field of illumination.

For example, multiple illumination beams are directed through a single diffractive element at different angles in order to provide an output illumination pattern reflective of the multiple beams and angular variation in the originating beams. In addition to the use of multiple illumination source beams, illumination can also be provided with multiple diffractive elements, where each diffractive element receives a subset of originating illumination beams to yield an associated pattern. In particular, because higher multiplex patterns emanating from a single diffractive element may provide excessive variation over an entire larger field of view, one may employ multiple diffractive elements each of which provide an illumination pattern over a subset of regions of a particular substrate, such that the illumination variability is confined to that which exists in a relatively small field of view, and thus does not exceed the ranges for a desired application.

Depending upon the density of reaction regions on a given substrate, flood illumination may comprise the use of a conventional laser beam or in some cases may employ beam expansion optics, in order to provide for the desired multiplex, by illuminating larger numbers of reaction regions with a single unified beam or spot. While effective at providing illumination over wide areas of a substrate upon which numbers of reaction regions are disposed, flood illumination can suffer from problems of inconsistent illumination intensity across the illuminated area. In particular, illumination intensity will tend to be greater at the center of a given beam, and drop off at the edges. Accordingly, different reaction regions will typically be subjected to differing illumination depending upon where in the illumination spot they fall. In addition, because the entire substrate area corresponding to the spot is illuminated, it can result in an inefficient use of applied radiation, e.g., wasted light that illuminates non-reaction regions thus requiring greater applied radiation than is necessary. Further, such flood illumination can present adverse effects of excess illumination, such as excess power consumption, reflected excitation light, autofluorescence of substrates as well as other optical components of the system, heating, and the like.

In other methods, a targeted illumination profile is used to preferentially illuminate multiple reaction sites simultaneously. For example, in one targeted illumination approach, an illumination beam is linearized to provide an illumination line that is capable of illuminating a number of discrete, co-linear regions on a substrate, simultaneously (See, e.g., International Patent Application Nos. US2007/003570 and US2007/003804, which are incorporated herein by reference in their entirety for all purposes), the full disclosures of which are incorporated herein by reference in their entirety for all purposes). By using multiple beams, or splitting a single beam before or after linearization, e.g., by passing the beam through a diffraction grating, one can create a number of parallel illumination lines in order to illuminate multiple rows of collinear reaction regions on a substrate. Such targeted illumination reduces the wasted illumination by not illuminating the space on the substrate between the illumination lines, and consequently reduces many of the issues associated with such excess illumination, as discussed previously. However, space between co-linear reaction regions, e.g., within a given row, is still illuminated, with the accompanying issues of wasted illumination and increased noise that results.

In further refinements, targeted illumination profiles use arrayed illumination spots that each illuminate a subset or a single discrete reaction region. This further enhances the signal to noise ratio, and increases illumination efficiency over linear illumination profiles, by only illuminating the spaces where illumination is desired, e.g., at and/or around the reaction regions. A number of optical configurations may be used to create these types of targeted illumination profiles, including, e.g., the use of lens arrays that focus individual illumination beams into multiple arrayed illumination spots, orthogonally oriented diffraction gratings that first split a single beam into a row of multiple beams, then split each of these beams into an orthogonally oriented row of additional beams, diffractive optical elements that convert a single beam into any of a variety of different targeted illumination profiles, including e.g., gridded arrays of illumination spots on a substrate (See, e.g., U.S. patent application Ser. No. 12/151,979, filed May 9, 2008, and PCT/US2008/05953, each of which are hereby incorporated herein by reference in its entirety for all purposes).

Dichroic Prism Array Illumination

One aspect of the invention is a device for illumination of a chip comprising an array of nanoscale regions or an array of patches of nanoscale regions. The device is a dichroic prism array (DPA) that divides a single incoming beam of laser light into multiple flood (non-beamlet) beams in order to illuminate a large ZMW chip. The dichroic face is designed to allow wavelengths of fluorescent light to pass through to collection optics. The design of the dichroic face may be eased and its performance improved by delivery laser light only of a particular polarization state, for example, linearly polarized. The invention has the ability to light large nanoscale region or ZMW chips without scaling up the size of illumination optics (except, for example, for total laser power). With this arrangement the length of the illumination optics is independent of the multiplex achieved on the ZMW chip. This allows an increase in ZMW multiplex without much attendant increase in instrument cost, except possibly for the cost of the laser, or size. For this arrangement, the delivery of illuminating light onto the ZMW is separate from the ZMW chip itself, allowing for independent production, troubleshooting, etc.

Typically, the nanoscale region, or ZMW chip would have a fused silica substrate. For example, the chip can comprise an array of ZMWs produced as nanoscale holes in an aluminum layer on a fused silica surface. The chip would typically include on-chip light concentrating features such as a micromirror or microlens for each ZMW. These light concentrating features serve the purposes of focusing the incoming flood illumination light onto the ZMWs, and roughly collimating the outgoing fluorescence light for more efficient fluorescence detection.

The DPA is well suited to be used to illuminate nanoscale region arrays in systems including compact lens trains (CLTs) described herein. For example, the array of dichroic prisms can be scaled such that each dichroic prism in a row will provide flood illumination light to a separate patch of ZMWs. As described elsewhere herein, CLTs can be packed together side by side in an array and ZMW multiplex is thus limited only by the size of the camera sensor and the length of the collection optics is independent of multiplex.

Figure 9:
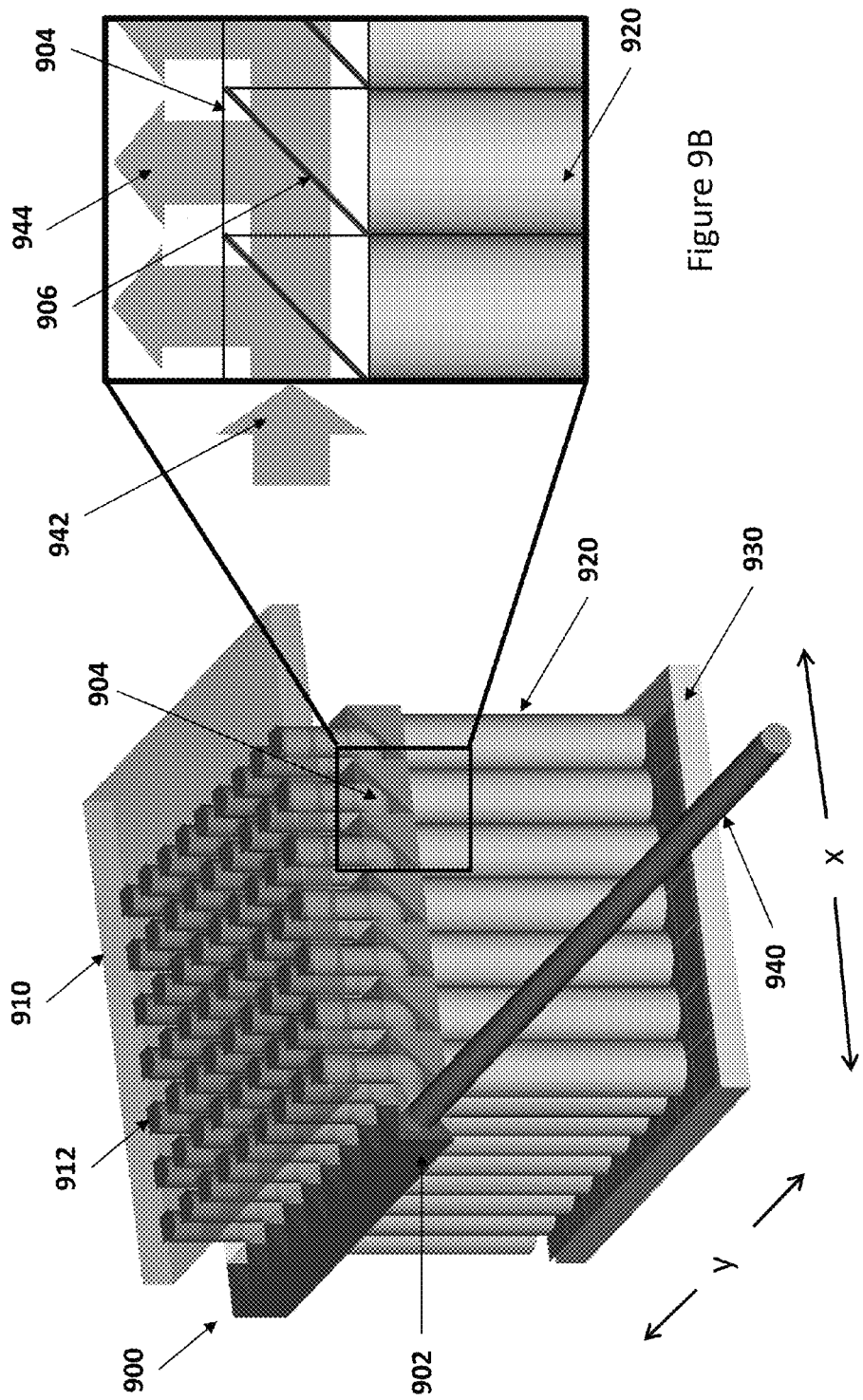
FIG. 9A shows a dichroic prism array of the invention for illuminating patches on a chip and allowing emitted light to enter a CLT array below to be directed onto a detector.
FIG. 9B shows an expanded view of the dichroic prism array illustrating the direction of portions of illumination light to patches on a chip.

That the DPA lends itself well for use with the array of CLTs can be seen in FIG. 9. FIG. 9A shows a DPA 900 used to illuminate a chip 910 having an array of patches of nanoscale regions or ZMWs 912. Each patch of nanoscale regions is illuminated from a dichroic prism below it. The illumination light can excite fluorophores in the nanoscale regions, producing emission. The emitted light from the nanoscale regions passes down, out of the chip 910, through the DPA, and into the CLT array below which spectrally separates the light and focuses it onto detector 930. In FIG. 9, the DPA array has 63 dichroic prisms. There is 9 by 7 array of patches of nanoscale regions (63 patches). Each patch has a dichroic prism below it providing illumination light, and each of those dichroic prisms has below it a CLT. In addition to the 63 dichroic prisms providing illumination light to the patches of nanoscale regions, there is a row of 9 beamlet splitting prisms or dichroic prisms (e.g. 902) which accepts illumination light 940 along the y axis. The row of prisms that are not under the patches of nanoscale regions can be, but need not be dichroic, as no emitted light needs to pass through them.

In FIG. 9A, a laser beam 940 enters a beamlet splitting prism, or dichroic prism 902. The laser beam can be, for example, a beam expanded to about a 1 mm diameter. Splitting prism 902 direct some of the light into a first row of 7 dichroic prisms (along the x axis), and allows the rest of the light to pass down the y axis to the next splitting prism. The light that is directed down the x axis passes into the first dichroic prism which reflects a fraction of the light upward to flood illuminate a patch of ZMWs above that dichroic prism. The remaining fraction of light travels onward down the x axis until it reaches the next dichroic prism, where again a fraction of the light is reflected upward to lights another patch of ZMWs. The relative amount of light that illuminates each patch in the array can be controlled by controlling the characteristics of the dichroic prism. For example, if one desires the same irradiance of light on each ZMW patch across the ZMW chip then the splitting fraction of each dichroic is systematically increased from one to the next. For example, a row of 7 dichroic prisms can be made with the fraction reflectances of about 1/7, 1/6, 1/5, 1/4, 1/3, 1/2, and 1.

In FIG. 9A, a first row of prisms (which need not be dichroic since no fluorescent light must pass through them) splits the single incoming beam into 9 equal beams which are sent into the DPA. Each of the beams is sent down a row of 7 dichroic prisms, each dichroic prism diverting a portion of the light to a patch above it. The 9 beams, each split again into 7 portions generates, and a total of 63 separate beams on the ZMW chip. The 63 prisms below the patches of ZMWs are typically dichroic to allow fluorescent light to pass from the ZMWs through them to the collection optics below. The DPA can be scaled to illuminate any suitable number of patches, and to send light into any suitable number of CLTs, including the numbers of patches and CLTs described herein. For example, the number of dichroic elements in the DPA can be from about 10 to about 1,000 or from about 50 to about 200.

The size of each beam may be tailored to fit the size of the ZMW patch on the ZMW chip. In the figure above, each ZMW patch is shown as having a gap around it and the beam lighting it would be sized accordingly. The size of the beam can be expanded to fill more of the area, even to where the beams are large enough to completely fill the chip with light. The DPA illumination system allows the size of the prism array to be set to fit the size of the ZMW chip and camera sensor while being fed by a single incoming illumination beam. This ability to scale the ZMW multiplex without much impact on the instrument illumination optics provides a significant benefit from this invention. Note that while the illumination geometry can remain the same for different illumination multiplex, the power in the incoming beam may need to be scaled to the level of ZMW multiplex.

The chip having the array patches of nanoscale regions can be produced, for example on a fused silica substrate. The nanoscale regions are typically zero mode waveguides having lateral dimensions of between 50 nm and 300 nm. The chip will typically include an array of focusing elements, one for each ZMW in order to direct the light effectively into the CLTs with minimal cross-talk. The focusing elements can be micro-lenses, which can be produced as binary lenses by semiconductor processing. In some cases, the focusing elements can comprise micromirrors.

In the design shown in FIG. 9A, the dimensions of the blocks containing the dichroic prisms can be, for example, 1.8×1.8 mm square. The CLT can have a square profile, or as shown, can be cylindrical, e.g. 1.8 mm diameter. The dichroic prism in this example is 1.8 mm cube. The system can be designed such that the presence of the dichroic prism does not significantly negatively impact the imaging quality of the collection path. The above design uses 63 dichroic mirrors and 63 CLTs. One advantage of the systems and devices of the invention is that it can be used with different numbers of CLTs packed into an array of arbitrary size.

FIG. 9B shows a close-up view of a portion of FIG. 9A illustrating how illumination light 942 traveling down the x axis passes into a dichroic prism comprising dichroic mirror 906. A portion of the light 944 is directed upward by the dichroic prism 904 to illuminate a patch of nanoscale regions such as ZMWs (not shown in FIG. 9B). The illumination light 944 causes excitation of fluorophores in the nanoscale regions which emit fluorescent light. The emitted light is at a different wavelength than the illumination light and passes through the dichroic prism 904 into the CLT 920 below.

Typically, the detector, CLT array, and DPA will all be part of an instrument, and the ZMW chip is expendable and brought to the correct position above the CLT and dichroic prism array. In some cases, the system can be used where there is no attempt to match the images from the nanoscale regions onto specific pixels on the detector. This approach has the advantage that the positioning of the chip is less critical, but this approach can be less effective at using the detector than an approach that matches the images of the nanoscale regions to specific pixels. If not attempting pixel matching, then lateral positioning is less critical. In some cases, the elements of z, tip, and tilt are adjusted to improve the quality of the focus across the chip. Where there is pixel matching, typically the chip should be positioned with the full 6 degrees of freedom.

The dichroic prism array (DPA) may be of various dimensions besides the 9×7 example given above. Its size can be chosen to match the size of the ZMW chip, and/or can be chosen tom match the size of the available sensor. The ability to size the optics to match the available sensor is another significant advantage of the approaches of the instant invention. When constructing an analytical instrument such as a nucleic acid sequencing instrument, the properties of the sensor are important, and the exact size of the sensor may be out of the direct control of the person building the analytical devices. In some cases the requirements of the analytical system will push the limits of available detectors, and it is desired to be able to incorporate new detectors as they become available.

The systems and devices of the invention allow for producing an optical system optimized for a particular detector size, and also to allow for upgrading the optical system to a new detector as they become available. The size of the beam striking the ZMW may be the same size or smaller than each individual dichroic prism. One aspect of the invention is the ability to control the size of the light beams contacting the chip. For example, one can save on total laser power and heat generation by sizing the beam to only fill the ZMW patch and not significantly illuminate the area outside of the ZMW patch. Although the DPA was described here as working in conjunction with an array of collection lens trains CLTs), the DPA can also be used with other types of collection optics including traditional single objective collection systems.

Figure 10:
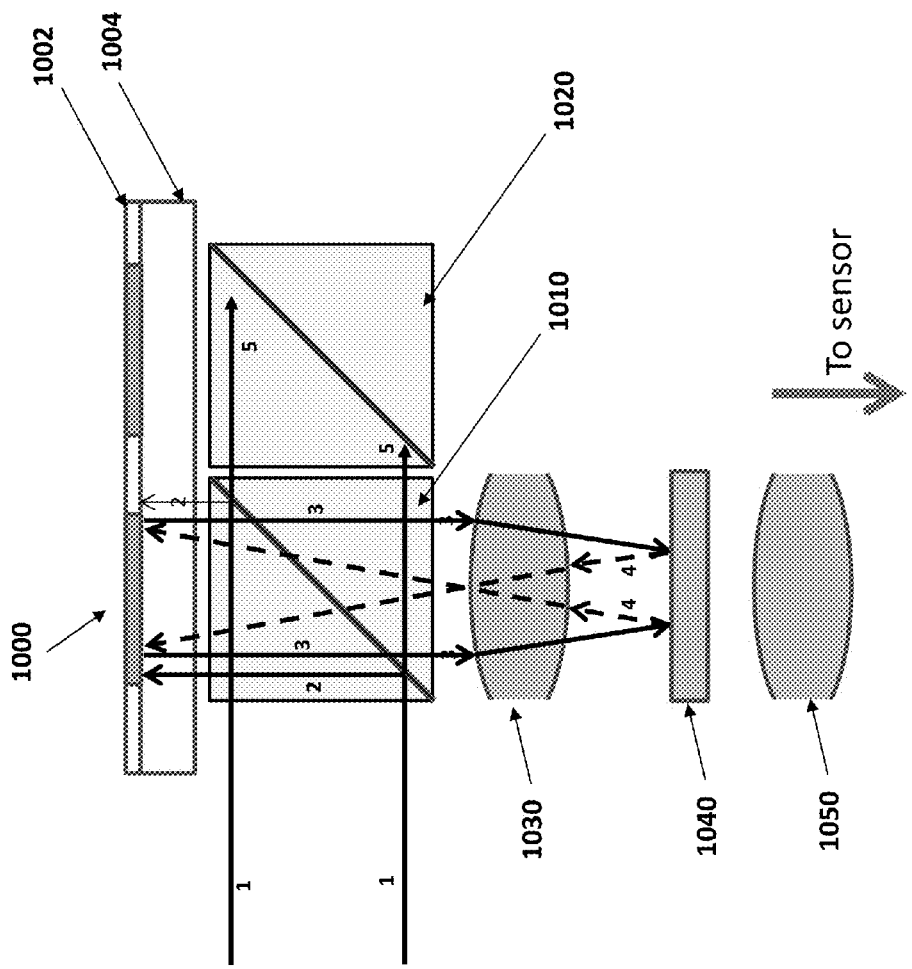
FIG. 10 shows ray tracing illustrating the performance of the DPA illumination system and illustrating the desirability in some cases to include an absorption filter to remove illumination light.

FIG. 10 shows ray tracing illustrating the performance of the DPA illumination system and illustrating the desirability in some cases to include a absorption filter to remove illumination light. A flood illumination beam 1 enters the first dichroic prism splitter 1010. The dichroic element in the dichroic prism reflects a portion of the illumination light 2 upward to the nanoscale region or ZMW chip 1000. The chip in the figure has a transparent substrate 1004, such as fused silica. In some cases, an opaque, e.g. silicon chip with windows to allow light to illuminate from below is used. On the top of the chip is a layer of nanoscale regions 1002. Where the nanoscale regions are ZMWs, the layer 1002 may comprise reflective aluminum.

The portion of the illumination light that is not directed up to the chip is allowed to pass through dichroic prism 1010 into dichroic prism 1020 (rays 5). The figure shows two dichroic prisms in a row. As described herein, DPAs can have many more prisms in the row and will typically have a number of rows.

Due to the reflective aluminum layer in the ZMW chip, a reflected beam travels downward with rays marked 3. A significant fraction of rays marked 3 can penetrate the dichroic prism (as it is intentionally only partially reflective) and will travel down toward the first collection lens group 1030 and to the laser rejection filter 1040.

In some aspects of the invention, the laser rejection filter 1040 is an absorption filter. This allows for rays 3 to be terminated by absorption at the laser rejection filter. Where a reflective laser rejection filter is used, rays 3 can reflect from the laser rejection filter and travel upward as rays marked 4 to reach the ZMW Chip. Such rays can create interference fringes with the main beam marked 2, which is typically undesirable. In some cases, the laser rejection filter 1040 rejects the light using a combination of absorption and reflection. In some cases a quarter wave plate can is provided between the DPA and the illumination light rejection filter.

Methods

The invention includes methods of carrying out analytical reactions using the optical arrays of the invention including arrays of compact lens trains and/or arrays of dichroic prisms. It will be understood by those of skill in the art from the description herein that the invention comprises the uses of any suitable combination of the optical components described herein to carry out analytical reactions. The methods of the invention include single molecule analyses including single-molecule binding reactions, for example as described in U.S. Pat. No. 7,315,019 and U.S. Published Application 2010/0323912 which are incorporated herein by reference for all purposes. The methods of the invention also include single molecule nucleic acid sequencing, which is described in more detail below.

In some aspects, the instant invention provides methods for measuring the emitted light from an array of patches of nanoscale regions. The patches of nanoscale regions can be, for example, arrays of zero mode waveguides. The methods typically use a chip having an array of patches of nanoscale regions where each patch of nanoscale regions has an array of nanoscale regions as described herein. Analytical reactions occur in the nanoscale regions resulting in the emission of light. The analytical reactions are configured to have at least two different light emitters, and light is emitted from the nanoscale regions from each of the emitters. There can be two, three, four or more different emitters, each emitting a different spectral range of light. These can be, for example, different fluorescent labels, each having a different set of emission wavelengths. The light from the emitters passes out of the bottom of the chip, typically through a lens array on the chip. Light from the chips passes into an emitted light collection system comprising an array of compact lens trains (CLTs). Each of the CLTs corresponds to a specific patch of nanoscale regions on the chip. The CLTs have a number of optic elements selected to effectively transmit the light from the chip onto a detector below the CLT. For example, each CLT will collimate light from the emission sources collimated with a collimating lens spectrally separate the light with a color separating element; and focus the light from onto a detector with a focusing lens. The light that is transmitted down to the detector with the CLT is detected by an array of pixels on the detector. Light corresponding to each of the two, three, four or more emitters is detected over time. The spectral separation function of the CLT results in directing images from different spectral regions to different sets of pixels on the detector. Thus the different sets of pixels on the detector are each sensitive to a different emitter. By monitoring the intensity at each of the sets of pixels over time, the analytical reactions corresponding to each of the labels can be monitored. In some cases, the analytical reaction is a nucleic acid sequencing reaction, and there are four florescent labels with spectrally distinct emissions, each corresponding to one of four types of nucleotide analog. The sequencing reaction can be carried out, for example, as described below.

While the CLT systems of the instant invention typically have a color separation component, in some cases the CLT can be made without a color separation component. For example, a CLT array can be used for single molecule sequencing using four different labels where each label has a different signal amplitude.

Single Molecule Sequencing

In the context of single molecule nucleic acid sequencing analyses, a single immobilized nucleic acid synthesis complex, comprising a polymerase enzyme, a template nucleic acid, whose sequence one is attempting to elucidate, and a primer sequence that is complementary to a portion of the template sequence, is observed to identify individual nucleotides as they are incorporated into the extended primer sequence. Incorporation is typically monitored by observing an optically detectable label on the nucleotide, prior to, during or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

Figure 11A:
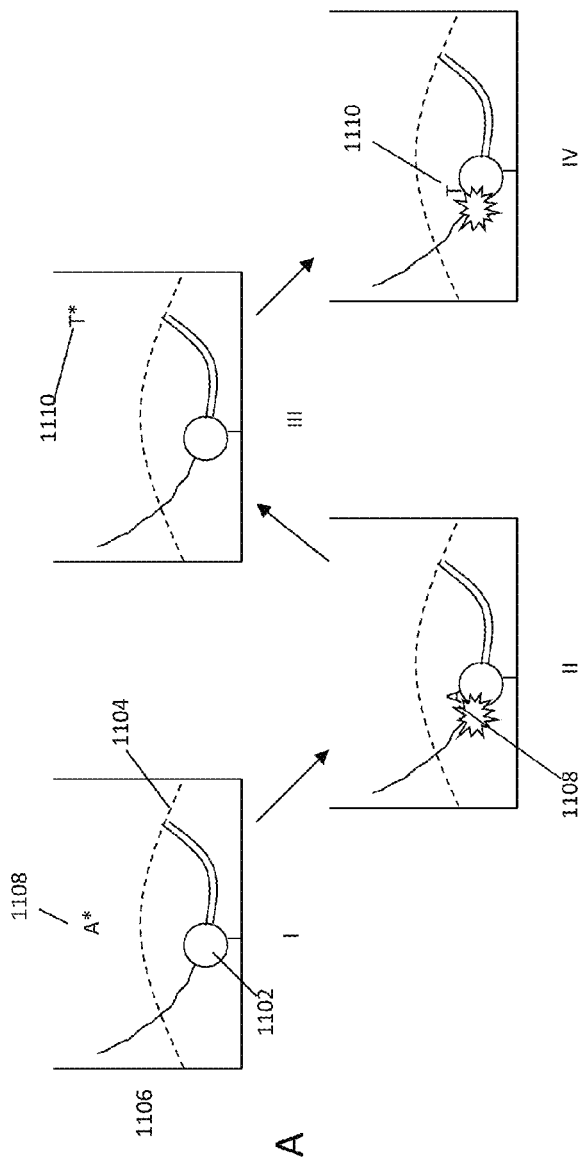
FIGS. 11A-11B show a schematic illustration of single molecule real time sequencing which can be carried out with the systems, devices, and methods of the invention.
Figure 11B:
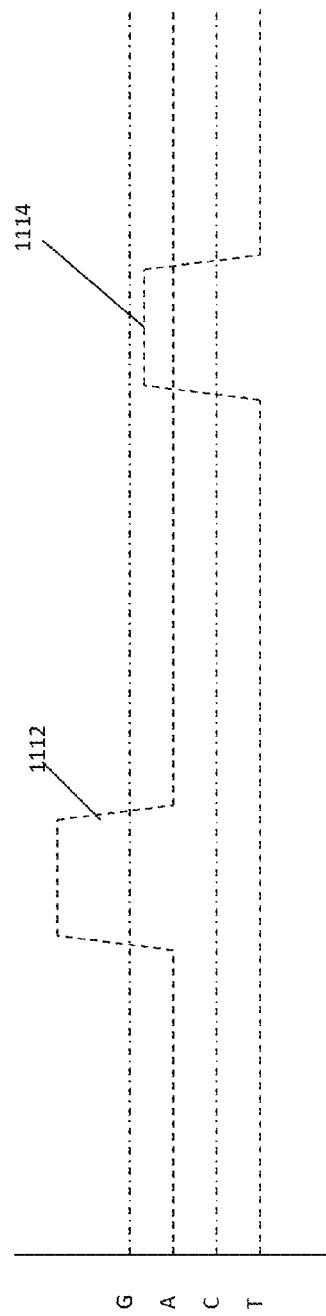

In another process, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase mediated template dependent primer extension reaction is monitored as it occurs. In preferred aspects, the template/polymerase primer complex is provided, typically immobilized, within an optically confined region, such as a zero mode waveguide, or proximal to the surface of a transparent substrate, optical waveguide, or the like (see e.g., U.S. Pat. Nos. 6,917,726, and 7,170,050 and Published U.S. Patent Application No. 2007-0134128, the full disclosures of which are hereby incorporated herein by reference in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated. A schematic illustration of this sequencing process is shown in FIG. 11. As shown in FIG. 11A, an immobilized complex 1102 of a polymerase enzyme, a template nucleic acid and a primer sequence are provided within an observation volume (as shown by dashed line 1104) of an optical confinement, of e.g., a zero mode waveguide 1106. As an appropriate nucleotide analog, e.g., nucleotide 1108, is incorporated into the nascent nucleic acid strand, it is illuminated for an extended period of time corresponding to the retention time of the labeled nucleotide analog within the observation volume during incorporation which produces a signal associated with that retention, e.g., signal pulse 1112 as shown by the A trace in FIG. 11B. Once incorporated, the label that attached to the polyphosphate component of the labeled nucleotide analog, is released. When the next appropriate nucleotide analog, e.g., nucleotide 1110, is contacted with the complex, it too is incorporated, giving rise to a corresponding signal 1114 in the T trace of FIG. 11B. By monitoring the incorporation of bases into the nascent strand, as dictated by the underlying complementarity of the template sequence, one can obtain long stretches of sequence information of the template. Further, in order to obtain the volumes of sequence information that may be desired for the widespread application of genetic sequencing, e.g., in research and diagnostics, higher throughput systems are desired.

By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments. In preferred aspects, the various different complexes are provided arrayed upon a substrate. Such arrayed complexes may be provided within optically or structurally confined structures, e.g., zero mode waveguides, or they may be patterned on a surface. Alternatively, they may be randomly disposed over a surface but subjected to targeted arrayed illumination, or detection, such that only complexes within an array pattern on the surface are monitored. For purposes of discussion herein, both configurations are referred to herein as the monitoring of arrayed complexes, or the like.

Analysis Systems

One aspect of the invention is an analysis system comprising the optical element arrays described herein. Analysis systems will include a socket or holder for holding a chip having an array of patches of nanoscale regions. The socket will typically have the capability of being aligned, for example in three to six degrees of freedom in order to orient the chip optically. As the chip will be in contact with the reaction fluid, the instrument will be designed to contain the fluid, and for example to control temperature and evaporation of the fluid. The analysis system will typically comprise the CLT array as described herein mated to a detector. The system provides power to the detector, and detector sends out electrical signals indicative of the light detected from the pixels.

The electrical signals from the detector are sent to a computing system having processors or computers that typically include information processors operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well-known computer networking or connecting methods, e.g., Firewire®, USB connections, wireless connections, WAN or LAN connections, or other connections that preferably include high aggregate data transfer rates. The computers also typically include software that analyzes the raw signal data, identifies signals that are likely associated with incorporation events, and identifies bases incorporated during the sequencing reaction, in order to convert or transform the raw signal data into user interpretable sequence data.

Further, the invention provides data processing systems for transforming raw data generated in an analytical reaction into analytical data that provides a measure of one or more aspects of the reaction under investigation, e.g., transforming signals from a sequencing-by-synthesis reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data; c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed, a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

In some aspects, the invention provides an analysis system for measuring emitted fluorescent light from an array of patches of nanoscale regions. The analysis system typically has (a) a holder for receiving a chip which has an array of patches of nanoscale regions in contact with a reaction fluid, and each patch of nanoscale regions has an array of nanoscale regions. The nanoscale regions emit fluorescent light from two, three, four, or more emitters, each emitter emitting a different spectral range of light, and each emitter indicative of a different component of an analytical reaction. The analysis system also has (b) an illumination system that provides excitation illumination to the nanoscale regions on the analysis chip, and (c) an emitted light collection system that has an array of compact lens trains or CLTs. Each CLT corresponds to a patch of nanoscale regions, and each CLT has a set of optical components for directing light from the chip down to the detector below the CLT. Each CLT will typically have: (i) a collimating lens for collimating light from the emission sources; (ii) a color separating element for spectrally separating light from the collimating lens; and (iii) a focusing lens for focusing light from the color separating element. The analysis system also has (d) a detector comprising an array of pixels onto which the focusing lens focuses light. The images of the nanoscale regions are focused onto the detector such that some pixels on the detector detect signal corresponding to the first spectral range, and some pixels on the detector detect signal corresponding to a second, third, fourth spectral range, or in some cases, more than four spectral ranges. The spectral separation in the compact lens trains allows for light from the different emitters to be detected over time by different sets of pixels on the detector. By monitoring each of the emitters in each of the nanoscale regions, the analysis system can measure the characteristics of many analytical reactions occurring at one time on the chip.

While the color element is typically described herein as separating collimated light, there are embodiments of the invention where the color separating element does not operate on light that has been collimated. For example, the color separation element can be part of the same element that does the collimation of light from the chip, or the color element can be part of the element that focuses light onto the detector.

The illumination is typically provided below the nanoscale regions, which can comprise zero mode waveguides. In some cases, the chip has waveguides incorporated into it for bringing the illumination light to the nanoscale regions. In some cases, the instrument further comprises a dichroic prism array that provides illumination light to the chip. The arrays of CLTs are typically provided as a set of lens plates, each with an array of optical elements. The plates are assembled in order to produce the CLT array.

EXAMPLES

CLT Arrays from Molded Plastic Optics

Figure 12C:
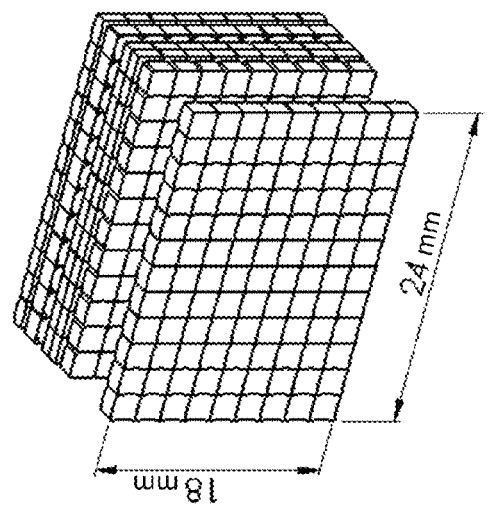
FIGS. 12A-12C show three embodiments of CLT arrays.
Figure 12B:
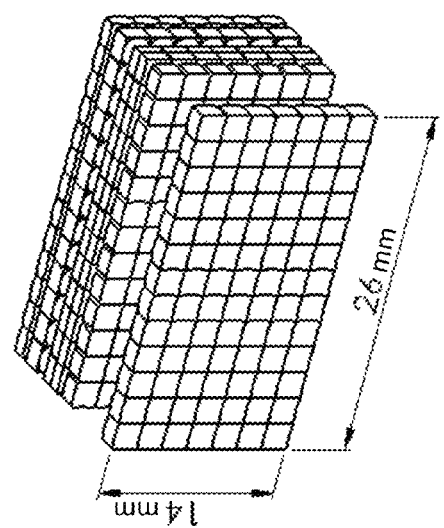
Figure 12A:
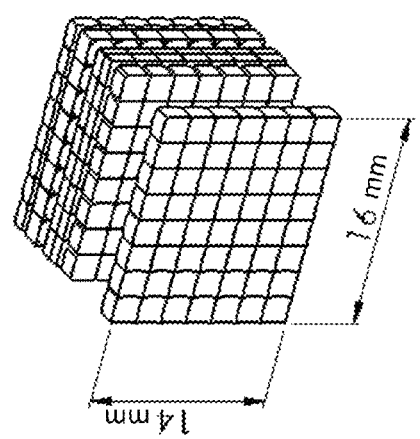

FIG. 12 shows three different embodiments of CLT arrays that are designed for use with three different detectors from various commercially available sensors. The ZMW chip and camera sensors are not shown. FIG. 12(A) utilizes sensor BAE 2521 from Fairchild, with an array of 7 by 8 CLTs with lateral dimensions of 14 mm by 16 mm. FIG. 12(B) uses a pair of BAE 2020 sensors from Fairchild butted side with an array of 7 by 13 CLTs with lateral dimensions of 14 mm by 26 mm. FIG. 12(C) uses the a Dynamax 0174 sensor with an array of 9 by 12 CLTs with lateral dimensions of 18 mm by 24 mm There is no direct matching of pixels to nanoscale region. Typically, about 3 spatial and about 4 spectral pixels for a total of 12 pixels are used per nanoscale region or ZMW. A BAE 2521 provides a multiplex of about 450 k ZMWs. Each lens train is 2×2 mm square. Larger sensors such as one constructed by butting two BAE 2020 sensors side by side provide about 700 k ZMWs. Butting two BAE 2521 sensors (not shown) provides about 920 k ZMWs. The Dynamax 0174, (FIG. 12(C)) services about 1.4M ZMWs. An analogous CLT array for observing 5 million ZMWs simultaneously utilizes 60 Megapixels at 12 pixels per ZMW, typically using more than one sensor. In the collection array schemes above the consumable ZMW chip has outer dimensions about the same as the camera sensor.

An all-plastic collection lens array element that services an island of about 8,000 ZMWs pitched on a 7.5×15 um rectangular grid is used in each case. The use of plastic optical elements allows for substantially reduced cost of the collection optics by molding. After molding, typically AR coatings and laser rejection coatings are added. The molded arrays of optical elements are stacked bonded together, and tested.

For the optical elements in the CLT, lens surface centering is typically kept to better than 5 um. Surface irregularity is typically controlled to a fraction of a micron. In some cases, these parts can be made directly from a fabricating mold. In other cases, further machining is done in order to meet the required tolerances. In some cases an extra layer is required in the lens train to compensate for accumulated errors Typical properties for the sensors used in the examples is shown in the Table below.

| Sensor | Pixel layout | Pixel Size | Peak QE | Read noise |
|---|---|---|---|---|
| Fairchild 2521 | 2160 × 2560 | 6.5 um | 56% | 1.5 e |
| Fairchild 2020 (dual, butted) | 2048 × 4096 | 6.5 um | 70% | 1.3 e |
| Dynamax 0174 | 4800 × 3600 | 5 um | 51% spec (55% typical) | 8 e |

Figure 13:
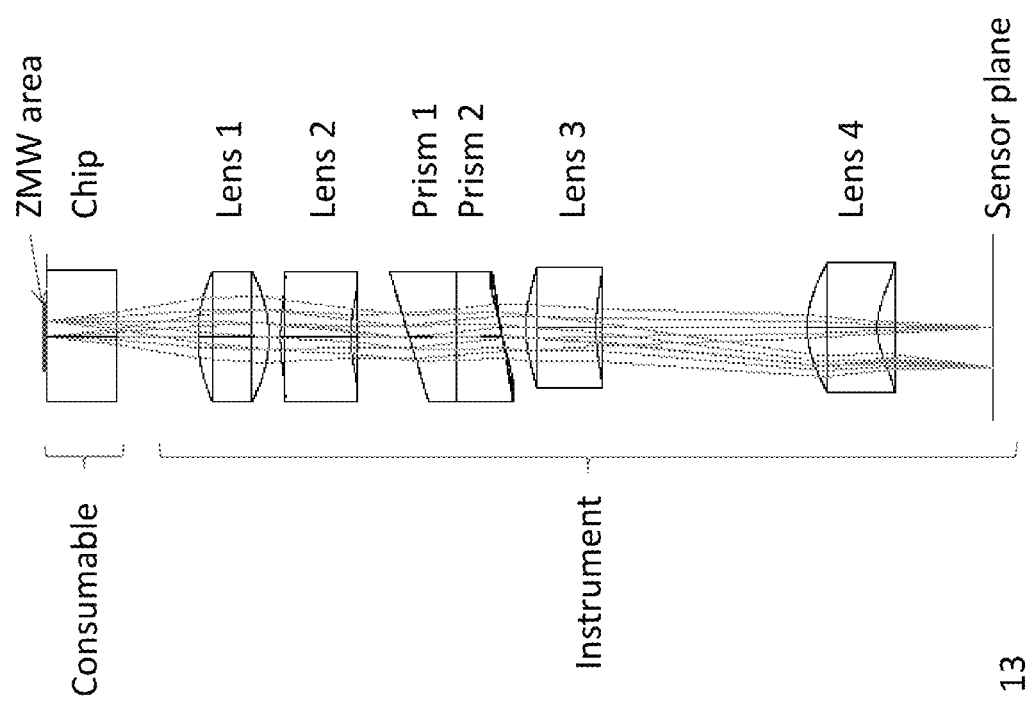
FIG. 13 shows a cross section of a single lens train viewed in isolation.

FIG. 13 shows a cross section of a single lens train viewed in isolation from the arrays of FIG. 12. Fluorescent light exiting the ZMWs is collimated by Lens 1 and Lens 2, which share that task. Lens 1 and lens 2 are fabricated from Zeonex E48R. Having four lens surfaces instead of two provides extra degrees of freedom and lower slopes which lead to better aberration control. A pair of prisms midway through the lens train separates the colors along one dimension of pixels. The use of two prisms rather than one enables the pair of prisms (together called the "wedge") to spread the light apart by wavelength without causing a change in direction of the center wavelength. The first prism is formed from Zeonex E48R, and the second prism if formed from Ultem. There is typically a jog in the rays from the wedge that requires decentering the downstream optical elements from the upstream ones.

An aperture stop can be positioned inside or above or below the wedge. The aperture controls the diameter of the light bundle that may pass through the lens train and also would help to control stray light from neighboring lens trains. Lens 3 and Lens 4 share the task of focusing the light onto the sensor. Lens 3 is formed from Zeonex E48R and lens 4 is formed from Ultem. The use of Ultem together with Zeonex E48R provides some control of axial color and field curvature. Several surfaces in the overall lens train are aspheric. The lens surfaces are coated for anti-reflection to increase transmission efficiency. Coatings are designed to block laser light that scatters from the ZMW chip and have a red wavelength cutoff to avoid having red light emitted from one ZMW fall onto the part of the sensor meant for the blue light emitted from a neighboring ZMW. In some cases, diffractive surfaces are included on one more lenses to improve axial and lateral color correction. Such diffractive surfaces are readily included in molded plastic parts.

The lenses in the CLT are typically made within the following tolerances.

| Tolerance Item | Limits |
| --- | --- |
| Surface Radii | +/−3 fringes |
| Irregularity | +/−1 fringes |
| Thicknesses | +/−10 microns |
| Surface and element decenters | +/−5 microns |
| Surface and element tilts | +/−0.05 degrees |

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

We claim:

1. An analytical system comprising:
an analysis chip comprising an array of patches, each of the patches comprising nanoscale regions that emit fluorescent light when illuminated;
a two-dimensional (x, y) array of dichroic prisms, each prism comprising a dichroic element that diverts illumination light up in the z dimension of the array to a patch on the analysis chip above it, wherein each dichroic element transmits fluorescent light emitted by the patch that it illuminates, whereby the emitted light from each patch passes down through each dichroic prism; and
a detector below the array of dichroic prisms that detects the transmitted fluorescent light.

2. The analytical system of claim 1 wherein the array of dichroic prisms comprises an array of prisms with N rows by M rows, the array of prisms further comprising a row of M beam splitting elements along an edge of the array of prisms, wherein illumination light is sent through the row of M beam splitting elements, and wherein each of the M beam splitting elements diverts a portion of the illumination light into a row of N dichroic elements, and each of the N dichroic elements in the row of N dichroic elements diverts a portion of light to the patch above it.

3. The analytical system of claim 1 wherein the number of dichroic prisms in the array is from about 10 to about 1,000.

4. The analytical system of claim 1 wherein the number of dichroic prisms in the array is from about 50 to about 200.

5. The analytical system of claim 1 wherein each patch of nanoscale regions comprises from about 1,000 to about 50,000 nanoscale regions.

6. The analytical system of claim 1 wherein the chip is in contact with a fluid sample comprising at least a first fluorescent species and a second fluorescent species, wherein the first fluorescent species can act as a first emitter when within or proximal to a nanoscale region, and the second fluorescent species can act as a second emitter when within or proximal to a nanoscale region.

7. The analytical system of claim 6 wherein the first and second fluorescent species comprise labeled nucleotide analogs.

8. The analytical system of claim 1 further comprising an array of color separating elements, the array comprising one color separating element for each dichroic prism.

9. The analytical system of claim 8 wherein the color separating element comprises a grating, a prism, or a grating prism.

10. A method for providing excitation illumination to an array of patches on a chip, wherein the patches emit fluorescent light, comprising:
providing, below the chip, a two-dimensional (x, y) array of dichroic prisms, each prism comprising a dichroic element;
sending excitation illumination light into the array of dichroic prisms such that each dichroic prism diverts illumination light up in the z dimension to a patch on the chip above it, stimulating fluorescent emission from the patches;
whereby the emitted light from each patch passes down through the dichroic prism that illuminated that patch to a detector.

11. The method of claim 10 wherein the array of dichroic prisms comprises an array of prisms with N rows by M rows, further comprising a row of M beam splitting elements along an edge of the array of dichroic prisms, wherein illumination light is sent through the M beam splitting elements, wherein each of the M beam splitting elements diverts a portion of the illumination light into a row of N dichroic elements, and each of the N dichroic elements in the row of N dichroic elements diverts a portion of light to the patch above it.

12. The method of claim 10 wherein the number of dichroic prisms in the array is from about 10 to about 1,000.

13. The method of claim 10 wherein the number of dichroic prisms in the array is from about 50 to about 200.

14. The method of claim 10 wherein the chip is in contact with a fluid sample comprising at least a first fluorescent species and a second fluorescent species, wherein the first fluorescent species can act as a first emitter when within or proximal to a nanoscale region, and the second fluorescent species can act as a second emitter when within or proximal to a nanoscale region.

15. The method of claim 14 wherein the first and second fluorescent species comprise labeled nucleotide analogs.

16. The method of claim 10 further comprising an array of color separating elements, the array comprising one color separating element for each dichroic prism.

17. The method of claim 16 wherein the color separating element comprises a grating, a prism, or a grating prism.

18. The method of claim 10 wherein each patch comprises from about 1,000 to about 50,000 nanoscale regions.

* * * * *